(12) United States Patent
Estes

(10) Patent No.: US 9,141,765 B2
(45) Date of Patent: *Sep. 22, 2015

(54) DISTRIBUTION OF INFUSION PUMPS

(71) Applicant: Asante Solutions, Inc., Sunnyvale, CA (US)

(72) Inventor: Mark C. Estes, Malibu, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/032,676

(22) Filed: Sep. 20, 2013

(65) Prior Publication Data

US 2014/0019158 A1    Jan. 16, 2014

Related U.S. Application Data

(63) Continuation of application No. 13/534,235, filed on Jun. 27, 2012, now Pat. No. 8,543,418, which is a continuation of application No. 12/369,534, filed on Feb. 11, 2009, now Pat. No. 8,234,126.

(60) Provisional application No. 61/027,869, filed on Feb. 12, 2008.

(51) Int. Cl.
*G06F 19/00* (2011.01)
*G06Q 50/22* (2012.01)

(52) U.S. Cl.
CPC ............ *G06F 19/3468* (2013.01); *G06Q 50/22* (2013.01)

(58) Field of Classification Search
USPC .......................................................... 705/2
See application file for complete search history.

(56) References Cited

U.S. PATENT DOCUMENTS

| | | |
|---|---|---|
| 3,858,106 A | 12/1974 | Launius |
| 6,248,093 B1 | 6/2001 | Moberg |
| 6,540,672 B1 | 4/2003 | Simonsen |
| 6,669,669 B2 | 12/2003 | Flaherty |
| 6,692,457 B2 | 2/2004 | Flaherty |
| 6,699,218 B2 | 3/2004 | Flaherty |
| 6,723,072 B2 | 4/2004 | Mahoney |
| 6,749,587 B2 | 6/2004 | Flaherty |
| 7,220,248 B2 | 5/2007 | Mernoe |
| 8,113,388 B2 | 2/2012 | Ophardt et al. |
| 2002/0050462 A1 | 5/2002 | Penney et al. |
| 2003/0088238 A1 | 5/2003 | Poulsen et al. |
| 2005/0171512 A1 | 8/2005 | Flaherty |
| 2005/0245878 A1 | 11/2005 | Mernoe et al. |
| 2005/0273059 A1 | 12/2005 | Mernoe et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0123819 A1 | 5/2007 | Mernoe et al. |
| 2007/0124002 A1 | 5/2007 | Mernoe et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173762 A1 | 7/2007 | Estes et al. |
| 2007/0179444 A1 | 8/2007 | Causey et al. |
| 2007/0185449 A1 | 8/2007 | Mernoe et al. |
| 2007/0203459 A1 | 8/2007 | Mernoe |
| 2007/0276329 A1 | 11/2007 | Mernoe |
| 2008/0045902 A1 | 2/2008 | Estes et al. |
| 2008/0045903 A1 | 2/2008 | Estes et al. |

(Continued)

*Primary Examiner* — John Pauls

(74) *Attorney, Agent, or Firm* — Fish & Richardson P.C.

(57) ABSTRACT

Some embodiments described herein provide for a number of portable infusion pumps to be distributed to a pump user via a pharmacy system or like.

14 Claims, 12 Drawing Sheets

(56) References Cited

U.S. PATENT DOCUMENTS

| | | |
|---|---|---|
| 2008/0045904 A1 | 2/2008 | Estes et al. |
| 2008/0045931 A1 | 2/2008 | Estes et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2009/0062730 A1 | 3/2009 | Woo |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |

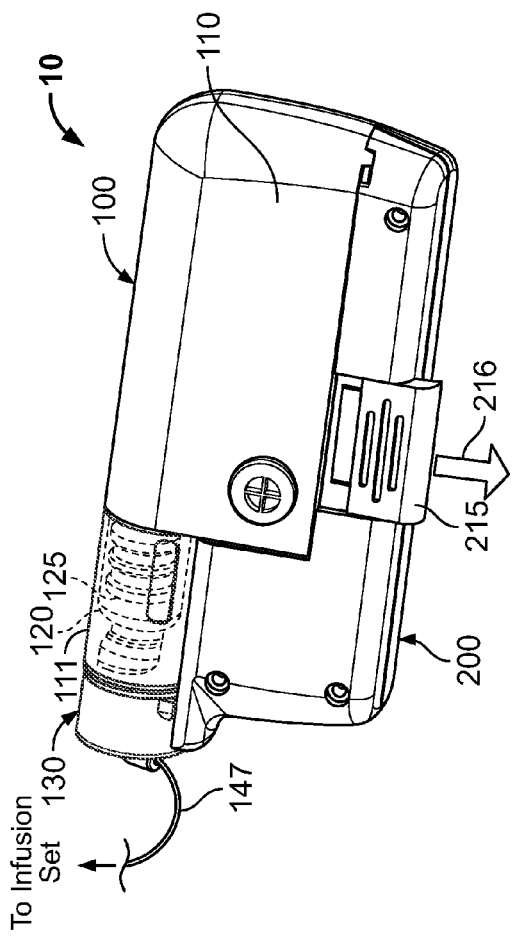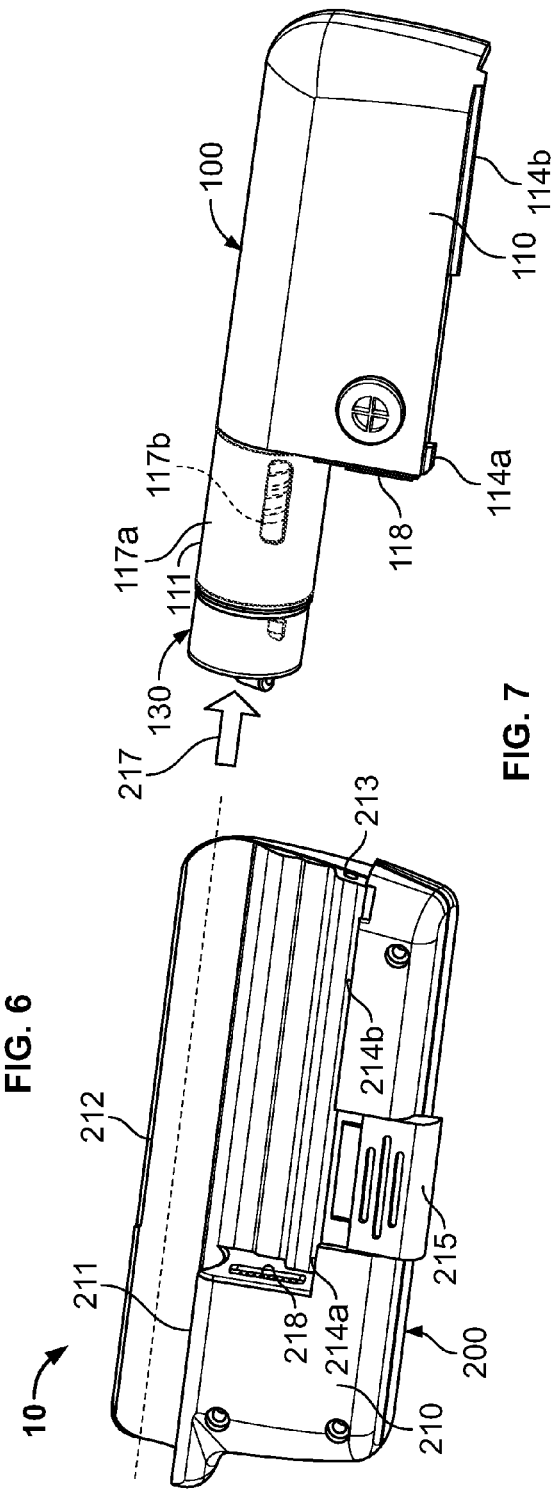

DISTRIBUTION OF INFUSION PUMPS

CROSS-REFERENCE TO RELATED APPLICATIONS

This application is a continuation of U.S. patent application Ser. No. 13/534,235 filed on Jun. 27, 2013, which is a continuation of U.S. patent application Ser. No. 12/369,534, filed on Feb. 11, 2009 (now U.S. Pat. No. 8,234,126), which claims priority to U.S. Provisional Patent Application Ser. No. 61/027,869, filed on Feb. 12, 2008. The complete contents of these earlier applications are hereby incorporated by reference.

TECHNICAL FIELD

This document relates to portable infusion pump systems to deliver fluids, such as insulin infusion pumps or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Some infusion pumps are provided to users as "durable medical equipment" that is intended to be used for many consecutive years. As such, the upfront costs of obtaining such an infusion pump are high. In some circumstances, a user's health insurance provider will pay a substantial portion of these upfront costs. However, the process for preauthorizing insurance coverage for an infusion pump (under the "durable medical equipment" procedure) may require a substantial burden of paperwork and communications among the pump supplier, the physician who prescribes the infusion pump for the user, and the user's health insurance provider.

SUMMARY

Some embodiments described herein provide for a number of portable infusion pumps to be distributed to a pump user via a pharmacy system or a like process that may impose a lower burden on the pump user when obtaining the infusion pump. In such circumstances, a pump user may simply pay a co-pay at the pharmacy window, and then take home a new supply of infusion pumps for use in dispensing a medicine (e.g., insulin or another infused medication) over a period of time. Accordingly, the paperwork burdens imposed upon the pump supplier and the physician treating the user may be reduced, and the delays associated with obtaining preauthorization for insurance coverage can also be reduced or eliminated. Furthermore, this distribution system may provide relief to health insurance providers by spreading the costs for the infusion pump usage over a longer period of time (rather than paying a large upfront cost for an infusion pump distributed as durable medical equipment).

In particular, embodiments, a method of receiving an insulin infusion pump device can include obtaining a prescription for a supply of infusion pump devices to deliver insulin. The method may also include submitting the prescription to a pharmacy for repeated deliveries of the infusion pump devices over a predetermined period of time. The method may further include receiving a plurality of infusion pump devices from the pharmacy contemporaneously with the receipt of insulin from pharmacy.

Some embodiments of a method of providing an insulin infusion pump device may include storing multiple infusion pump devices in a pharmacy inventory. The method may also include, in response to an individual user request to a pharmacy for repeated deliveries of infusion pump devices, distributing a plurality of infusion pump devices from the pharmacy inventory to the individual user while contemporaneously distributing insulin from the pharmacy inventory.

In certain embodiments, a method of providing an insulin infusion pump system can include selecting a predetermined ratio of disposable and non-reusable infusion pump devices to insulin cartridges that are operable to be received in the infusion pump devices. The predetermined ratio may one infusion pump device to one insulin cartridge. The method may also include arranging disposable pump devices and insulin cartridges into a package according to the predetermined ratio. The method may further include providing the package to a requestor in response to a request.

In some embodiments, a method providing an insulin infusion pump system may include obtaining a disposable and non-reusable infusion pump device, an insulin cartridge containing insulin, and at least one infusion set device operable to penetrate into skin. The method may also include arranging the disposable pump device, the insulin cartridge, and the at least one infusion set device into a single package. The method may further include providing the single package to a requestor in response to a request for at least the pump device.

Some or all of the embodiments described herein may provide one or more of the following advantages: First, a pump user can receive a supply of portable infusion pumps in a manner that can reduce the time and paperwork burden for the user. For example, the individual user can receive a number of portable infusion pumps via a pharmacy system or the like so that the pump user can simply pay a relatively small fee at the pharmacy window to obtain a supply of infusion pumps. Second, the distribution of the infusion pumps via a pharmacy system may provide benefits to health insurance providers by spreading the costs for the infusion pump usage over a longer period of time. For example, each of the infusion pumps can be a low cost and disposable component, so the cost to insurers is spread out in the form of user prescription refills, as opposed to a large up front cost. By spreading the costs over a greater period of time, the health insurance provider is not necessarily exposed to a sunk cost in the form of the large upfront payment in the event that the pump user decides to no longer continue pump therapy or accidentally loses or damages the infusion pump. Third, the pharmacy distribution of the infusion pumps can reduce the substantial paperwork burdens that may otherwise be required for preauthorization of insurance coverage for an infusion pump classified as "durable medical equipment." In these circumstances, the paperwork burdens imposed upon the pump supplier and the physician treating the user may be reduced, and the delays associated with obtaining preauthorization for insurance coverage can also be reduced or eliminated. Fourth, one or more of the infusion pumps can be packaged along with an associated medicine cartridge to simply the transaction for the pump user. For example, the package may include a quantity of infusion pumps in a 1:1 ratio with the quantity of medicine cartridges. In addition, the package may include a quantity of infusion sets for use with one or more of the infusion pumps. In such circumstances, the pump user may be able to pay a single copay or other fee to receive the package containing the infusion pumps, the medicine cartridges, and other components.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6-7 are perspective views of a pump device being detached from a controller device, in accordance with some embodiments.

Like reference symbols in the various drawings indicate like elements.

DETAILED DESCRIPTION OF ILLUSTRATIVE EMBODIMENTS

Figure 1:
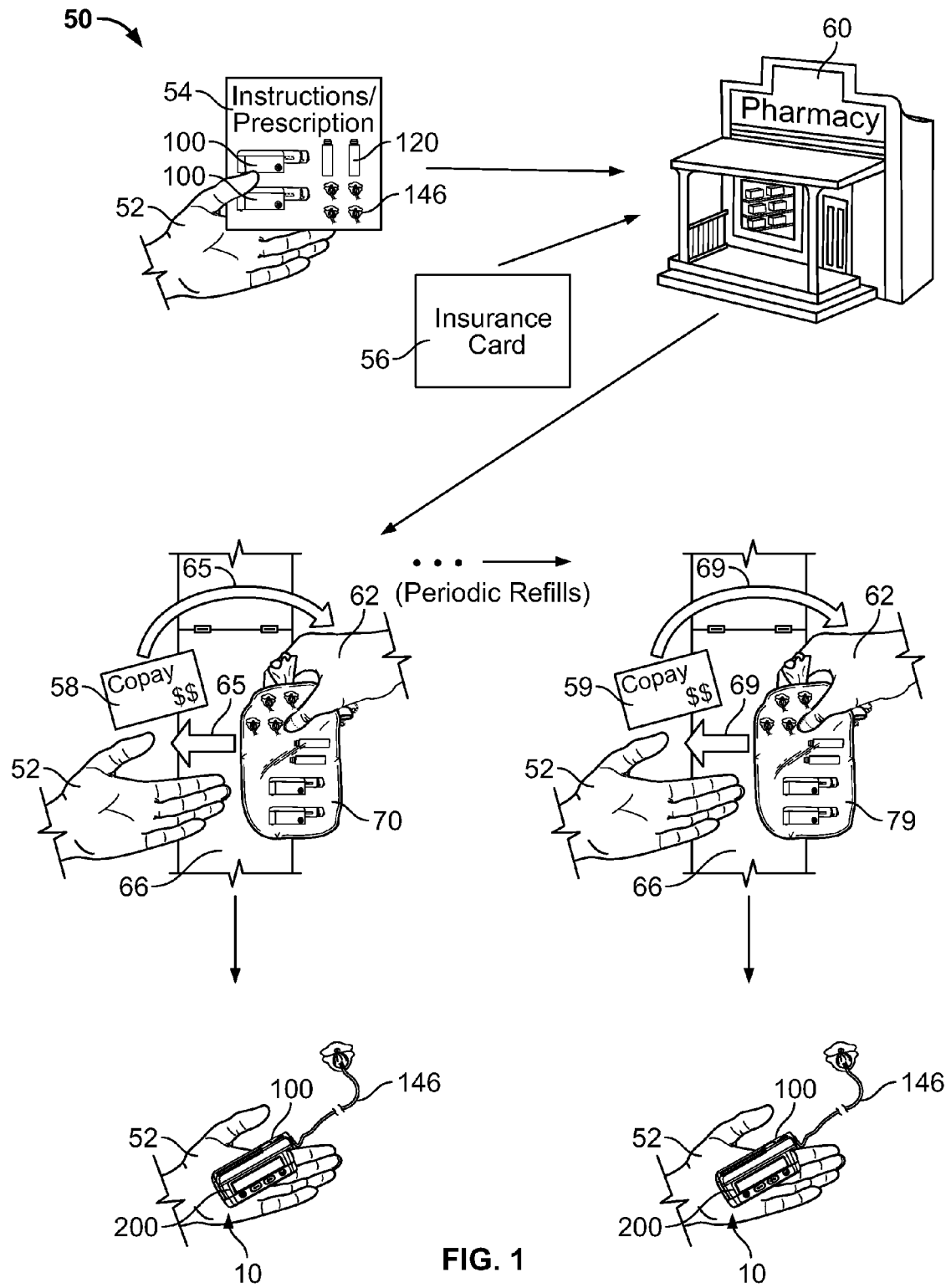
FIG. 1 is a diagram of distributing infusion pumps in accordance with some embodiments.

Some embodiments described herein enable an infusion pump user to obtain a supply of portable infusion pumps in a manner that can reduce the time and paperwork burden for the user. In particular, a number of portable infusion pumps to be distributed to the individual user via a pharmacy system or the like so that the pump user can simply pay a relatively small fee at the pharmacy window to obtain a supply of infusion pumps without burdensome applications, reimbursement requests, or other time-consuming paperwork. Also, the pump user may experience less delay between the time of the prescription and the time of starting pump therapy because the paperwork burdens normally imposed upon the pump supplier and the treating physician (e.g., paperwork required for preauthorization of "durable medical equipment") may be eliminated or reduced. Furthermore, the distribution methods described herein may provide relief to health insurance providers by spreading the costs for the infusion pump usage over a longer period of time.

For example, some processes described herein permit an individual to obtain one or more infusion pumps and associated components (e.g., medicine cartridges, infusion sets, and the like) in a convenient manner at a single location during a single visit. In particular embodiments, a pump user can obtain a set of infusion pumps, medicine cartridges that correspond to the infusion pumps, and other components from a pharmacy (e.g., a brick and mortar establishment, or direct order system) by providing the pharmacy with information related to the individual's insurance and providing the pharmacy with a copay payment. The infusion pumps may be, in some embodiments, disposable and non-reusable components that made available to the pump user from the pharmacy at the same time that medicine cartridges are obtained. Optionally, the entire package can be obtained using a single copay payment. In this manner, an individual can travel to a pharmacy, present a prescription and insurance card, complete a single payment transaction, and thereby receive one or more infusion pumps and other components for use in a wearable infusion pump system. In another example, an individual could receive the infusion pumps, medicine cartridges, and other components via a direct pharmacy order system. In this case, as with the pharmacy visit, a lower paperwork burden is imposed on the individual requesting the infusion pumps, but also has the additional advantage of having the components shipped directly to the individual's address. In these scenarios, health insurance providers can also benefit. For example, in some embodiments the infusion pump can be a low cost and disposable component, so the cost to insurers is spread out over a greater period of time (e.g., in the form of refills), as opposed to a large up front cost. Thus, the risks to the health insurance provider can be reduced. If, for example, the pump user decides to no longer continue pump therapy or accidentally loses or damages the infusion pump, the health insurance provider is not necessarily exposed to a sunk cost in the form of the large upfront payment.

Referring now to FIG. 1, in some embodiments of an infusion pump distribution system 50 a customer 52 (e.g., a pump user or the like) submits information to a pharmacy 60. For example, the information may include a medical prescription 54 from a health care professional for infusion pumps 100. The prescription 54 can be a written prescription that was previously obtained by the customer 52 from a medical professional. It should be understood that, in some embodiments, the prescription 54 may include written instructions from a medical professional for the use of components that do not require a formal written prescription. In this embodiment, the prescription 54 includes instructions for one or more infusion pumps 100, one or more medicine cartridges 100, and one or more infusion sets 146. Optionally, the customer 52 may also submit information to the pharmacy 60 describing insurance coverage, such as an insurance card 56. The insurance card 56 may assist the pharmacy in determining what portion of the costs will be paid by a covering insurance company and what portion of the cost will be paid by the customer 52 in the form of a copay payment. Upon receipt of the information from the user 52, the pharmacy 60 may verify the information contained in one or both of the presented prescription 54 and insurance card 56. For example, the pharmacy 60 can contact the medical professional who issued the prescription 54 to verify the validity of the prescription 54. Also, the pharmacy 60 can contact the insurance company that issued the health insurance card 56 to determine the existence and extent of existing coverage.

In some embodiments, after preliminary steps have been completed (e.g., after the previously described information is submitted to the pharmacy 60), a pharmacist 62 can enter into a transaction 65 with the customer 52. This transaction 65 can include, for example, the payment of a copay 58 (e.g., using cash, credit card, check, and the like) by the customer 52 to the pharmacist 62 (e.g., a licensed pharmacist or any other employee of the pharmacy 60) at a pharmacy counter 66. During the transaction 65, the pharmacist 62 can provide to the customer 52 a container 70 (e.g., a bag or other package) including one or more infusion pumps 100 (as indicated by the prescription 54) and other components. In this embodiment, the infusion pump components in the container 70 include two or more disposable and non-reusable pump devices 100 for use with a wearable insulin pump system, two or more medicine cartridges 120, and a plurality of infusion sets 146. Also in this embodiment, the number of medicine cartridges 120 may be provided in a 1:1 ratio with the number of infusion pumps 100 so that each pump 100 can be used with one medicine cartridge 120. In these examples, the user can obtain from the pharmacy 60 the two pump devices 100, the two medicine cartridges 120, and the four infusion sets 146 in a single transaction 65. This transaction 65 can be accomplished with a single copay payment 58 in some circumstances. In other embodiments, the number of cartridges 120 and infusion sets 146 need not be related to the number of pump devices 100. The number of components provided at the transaction 65 can be based on a number of factors, such as the type and severity of the user's condition to be treated, the type(s) of medicament to be delivered, the style of infusion sets 146 to be used, and the like.

Still referring to FIG. 1, in some embodiments the user 52 can refill the prescription 54 at the pharmacy 60 over a period of time. When the prescription 54 is written, the medical professional can indicate on the prescription 54 a maximum number of times (e.g., five, ten, twelve, or the like) that the prescription 54 can be refilled or the maximum duration of time in which refills can be obtained. Accordingly, the user 52 can initiate a refill transaction 69 in which the user 52 indicates the prescription 54 to be refilled and provides a refill copay payment 59. In response, the user 52 can receive from the pharmacist 62 a container 79 (e.g., a bag) containing one or more components listed on the prescription 54. In cases where the prescription is refillable, the pharmacy 60 can maintain records containing information related to the prescription 54 and the insurance card 56 in anticipation of future visits by the customer 52. Thus, the customer 52 can supply the pharmacist 62 with the refill copay payment 59, but may not be required to provide a new written prescription or the insurance card 56 in order to receive the container 79. The pharmacy 60 can keep track of how many times the prescription 54 is refilled and may stop refilling the prescription 54 once the number of refills or refill time period exceeds the maximum allowed. Thereafter, the customer 52 can contact a medical professional to obtain a new prescription.

After each transaction 65 or refill transaction 69, the user 52 can employ the infusion pump(s) 100 to infuse the medicine in the cartridge(s) 120 through the infusion sets 146. In this embodiment, the infusion pump device 100 comprises a disposable one-time-use pump that is part of a portable system 10 (described in more detail below). In particular, each pump device 100 can be attached with a reusable controller device 200 (described in more detail below) to activate the pump drive system in the infusion pump device 100.

In some embodiments, the individual that presents the prescription 54, insurance card 56, and the copay 58 is also the pump user of the assembled infusion pump system 10. It should be understood from the description herein that the pump user can provide the information and complete the transactions 65 and 69 using an agent or proxy (e.g., friends, family members, and the like). Additionally, although FIG. 1 depicts the user 52 as going to a pharmacy building, it should be understood that the pharmacy 60 may comprise a direct order system. In one example, a user 52 could submit (via phone or Internet) the information listed on the prescription 54 and the insurance card 56 to a service operator, along with an electronic copay 58 (e.g., credit card, e-check, or the like). After supplying the information in this manner, the user 52 can then choose to travel to a pharmacy building or elect to have the components shipped directly to the user's address (e.g., at home, at work, or the like).

Figure 2:
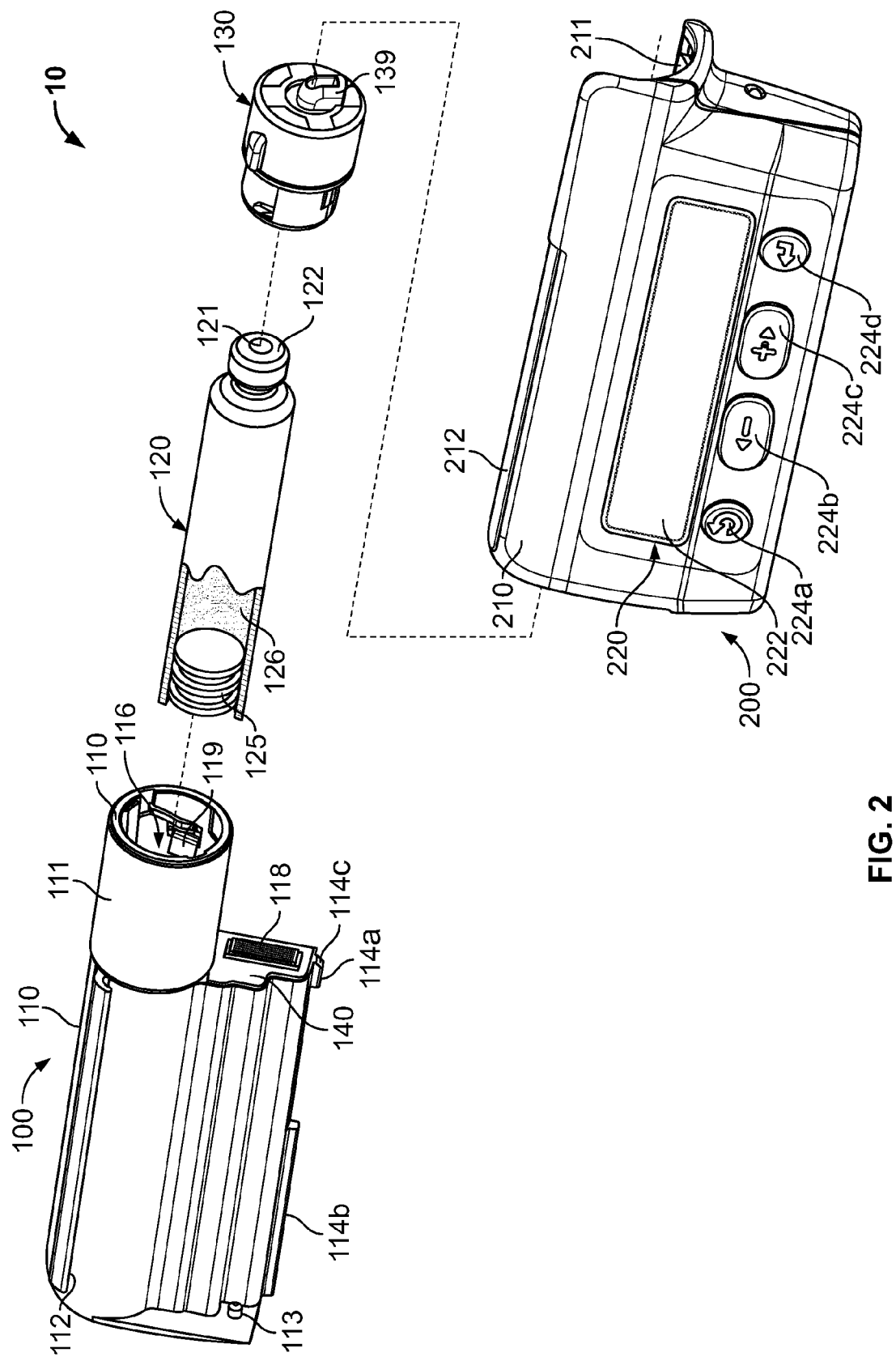
FIG. 2 is a perspective view of an infusion pump system in accordance with some embodiments.
Figure 3:
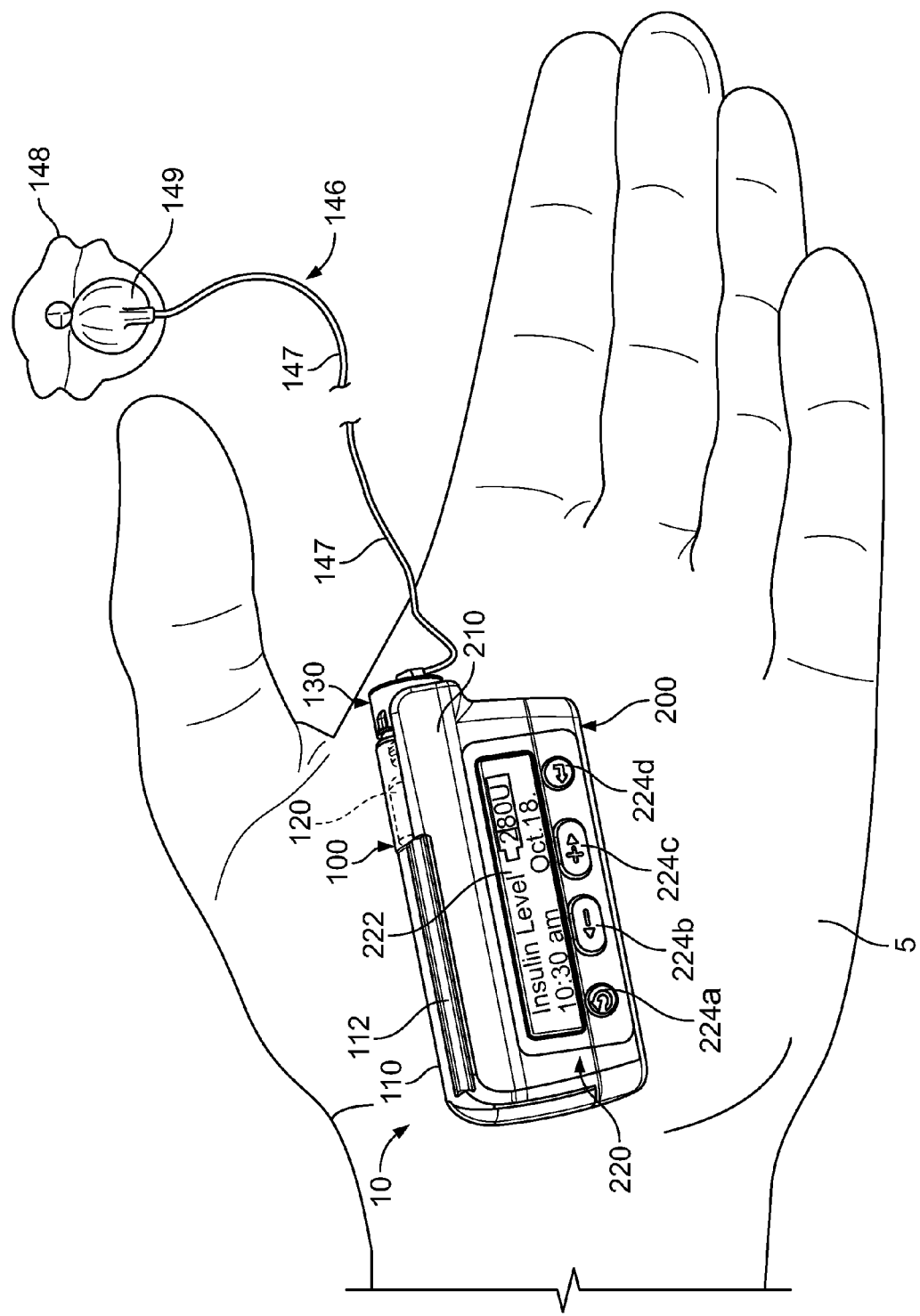
FIG. 3 is a perspective view of an infusion pump system in accordance with particular embodiments.

Referring now to FIGS. 2-3, some embodiments of the infusion pump system 10 can include a disposable pump device 100 and a reusable controller device 200 that can communicate with the pump device 100. The pump device 100 can include a housing structure 110 that defines a cavity 116 in which the fluid cartridge 120 can be received. The pump device 100 also can include a cap device 130 to retain the fluid cartridge 120 in the cavity 116 of the housing structure 110. The pump device 100 can include a drive system (described in more detail below) that advances a plunger 125 in the fluid cartridge 120 so as to dispense fluid therefrom. The controller device 200 can communicate with the pump device 100 to control the operation of the pump's drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

Figure 8:
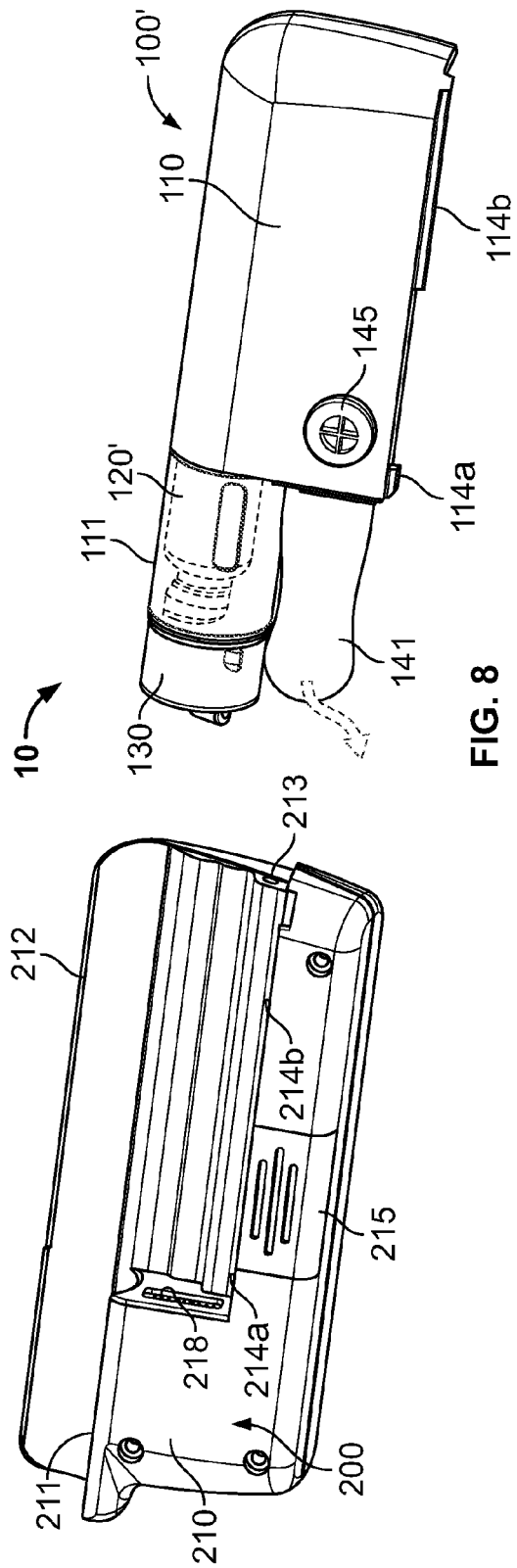
FIGS. 8-9 are perspective views of the pump device of FIGS. 6-7 being discarded and the controller device of FIGS. 6-7 being reused with a new pump device.

The controller device 200 may be configured as a reusable component that provides electronics and a user interface to control the operation of the pump device 100. In such circumstances, the pump device 100 can be a disposable and non-reusable component that is discarded after a single use. For example, as described in more detail below in connection with FIGS. 6-11, the pump device 100 can be a "one time use" component that is thrown away after the fluid cartridge 120 therein is exhausted. Thereafter, the user can removably attach a new pump device 100' (having a new medicine cartridge 120' as shown in FIG. 8) to the reusable controller device 200 for the dispensation of fluid from the new fluid cartridge 120'. Accordingly, the user is permitted to reuse the controller device 200 (which may include valuable electronics or data) while disposing of the relatively low-cost pump device 100 after each use. Such a pump system 10 can provide enhanced user safety as a new pump device 100 (and drive system therein) is employed with each new fluid cartridge 120. Moreover, such a pump system 10 can provide the user with an opportunity to obtain a plurality of the pump devices 100 at the pharmacy 60 (FIG. 1) while also obtaining the prescribed medicine (e.g., in the cartridges 120).

Briefly, in use, the pump device 100 can be configured to be removably attached to the controller device 200 in a manner that provides a secure fitting, an overall compact size, and a reliable electrical connection that is resistant to water migration. For example, as described in more detail below in connection with FIGS. 6-11, the controller device 200 can include a housing 210 having a number of features that mate with complementary features of the pump housing 110. In such circumstances, the controller device 200 can be removably attached to the pump device 100 in a generally side-by-side configuration while not fully surrounding the pump housing 110. Accordingly, in this embodiment, the pump device 100 and the controller device 200 can be separate components that fit together in a compact manner. The compact size permits the infusion pump system 10 to be discrete and portable (as described below in connection with FIGS. 4-5). Moreover, at least one of the pump device 100 or the controller device 200 can include a release member that facilitates an easy-to-use detachment and replacement process.

Still referring to FIGS. 2-3, the pump system 10 can be a medical infusion pump system that is configured to controllably dispense a medicine 126 (FIG. 2) from the cartridge 120. As such, the fluid cartridge 120 can contain the medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received). In those circumstances, the user may receive vials of the medicine from the pharmacy 60 (FIG. 1) in order to fill the reservoir, or the pump devices 100 may be prefilled with the medicine before the user obtains the pump devices 100.

In some embodiments, the pump device 100 can include one or more structures that interfere with the removal of the medicine cartridge 120 after the medicine cartridge 120 is inserted into the cavity 116. For example, as shown in FIG. 2, the pump housing structure 110 can include one or more retainer wings 119 that at least partially extend into the cavity 116 to engage a portion of the medicine cartridge 120 when the medicine cartridge 120 is installed therein. For example, after the medicine cartridge 120 is inserted to a particular depth, the retainer wings 119 are biased to flex outward (toward the center of the cavity 116) so that the retainer wings 119 engage a neck portion 129 of the medicine cartridge 120. Such a configuration may facilitate the "one-time-use" feature of the pump device 100. In some embodiments, the retainer wings 119 interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 2-3, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system 300 (not shown in FIGS. 1-3, refer to FIG. 13) of the pump device 100. As described in more detail below, the pump device 100 can include a drive system that causes controlled dispensation of the medicine or other fluid from the cartridge 120. In some embodiments, the drive system incrementally advances a piston rod (not shown in FIGS. 2-3) longitudinally into the cartridge 120 so that the fluid is forced out of an output end 122. A septum 121 (FIG. 2) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 can communicate electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

As shown in FIG. 2, the pump device 100 can include an electrical connector 118 (e.g., having conductive pads, pins, and the like) that are exposed to the controller device 200 and that mate with a complementary electrical connector (refer to connector 218 in FIG. 7) on the adjacent face of the controller device 200. The electrical connectors 118 and 218 provide the electrical communication between the control circuitry (refer, for example, to FIG. 12) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. Furthermore, the infusion pump system 10 can include a gasket 140 that provides a seal around the electrical connector interface to thereby resist migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

In some embodiments, the pump device 100 may be moved in a longitudinal direction toward the controller device 200 until one or more structures connect and secure the separate components in the side-by-side arrangement. For example, the controller device 200 includes a controller housing structure 210 having a number of features that are configured to mate with complementary features of the pump housing structure 110 so as to form a releasable mechanical connection. In the embodiment shown in FIG. 2, the pump housing structure 110 includes a barrel 111 that mates with a complementary barrel channel 211 of the controller housing 210. Also, the pump housing 110 includes slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 may include a segmented rail 114a-b that mates with a guide channel 214a-b (FIG. 7) to direct the relative longitudinal motion between the pump device 100 and the controller device 200. As described in more detail below, the segmented rails 114a-b may interact with a release member 215 (FIG. 7) so as to releasably secure the pump device 100 into assembly with the controller device 200. In addition, the pump housing 110 may include an extension 113 that mates with a depression 213 (FIG. 7) in the controller housing 210 when the pump device 100 is fully attached to the controller device 200.

Still referring to FIG. 2, when the pump device 100 is advanced in the longitudinal direction toward the controller device 200 as guided by the slider channel 112 and the segmented rails 114a-b, the electrical connector 118 of the pump device 100 is directed toward engagement with the mating connector 218 (FIG. 7) of the controller device 200. As the connectors 118 and 218 join together to form the electrical connection, the release member 215 (FIG. 7) is shifted to a position between the segmented rails 114a-b so as to prevent withdrawal of the connection. Also, when the connectors 118 and 218 are mated, the extension 113 and barrel 111 are mated with the corresponding depression 213 (FIG. 7) and barrel channel 211 so as to resist relative rotational movement between the pump device 100 and the controller device 200. In this embodiment, the physical attachment of the electrical connectors 118 and 218 may also serve to resist relative rotational movement between the pump device 100 and the controller device 200. Furthermore, when the connectors 118 and 218 are mated, the slide channel 112 is mated with the corresponding rail 212 and barrel channel 211 so as to resist relative side-to-side movement between the pump device 100 and the controller device 200.

Also, when the connectors 118 and 218 join together to form the electrical connection, the gasket 140 is compressed between the adjacent surfaces of the pump housing 110 and the controller housing 210. The gasket 140 may comprise a polymer foam material that is adhered to a surface of either the pump housing 110 or the controller housing 210 (e.g., adhered to the pump housing 110 in this embodiment). The gasket 140 may be die cut to a selected shape so as to include an aperture for the electrical connection. Thus, in this embodiment, the gasket 140 surrounds the electrical connection when the pump device 100 is secured to the controller device 200. The configuration provides protection from water migration to one or both of the electrical connectors 118 and 218. Accordingly, in particular circumstances, the infusion pump system 10 can be assembled into a "water tight" configuration that protects sensitive internal components from water migration in the event that the user encounters water while wearing the pump system 10.

Additionally, in some embodiments, the attachment of the pump device 100 to the controller device 200 can be accomplished by a user with a convenient "one-movement" process. For example, as previously described, the user can readily slide the pump device 100 and the controller device 200 toward one another in a single movement (e.g., in the longitudinal direction) that causes both a physical connection and an electrical connection. As described in more detail below in connection with FIGS. 6-11, the release member 215 may be arranged so as to automatically adjust to a locked position when the pump device 100 is advanced into engagement with the controller device 200. Thus, the infusion pump system 10 permits users to readily join the pump device 100 and the controller device 200 without compound or otherwise difficult hand movements—a feature that can be beneficial to child users or to elderly users.

It should be understood that, in other embodiments, other features or connector devices can be used to facilitate the side-by-side mounting arrangement. These other features or connector devices may include, for example, magnetic attachment device, mating tongues and grooves, mounting protrusions that friction fit into mating cavities, or the like.

Still referring to FIGS. 2-3, the controller device 200 can include a user interface 220 that permits a user to monitor the operation of the pump device 100. In some embodiments, the user interface 220 includes a display device 222 and one or more user-selectable buttons (e.g., four buttons 224a, 224b, 224c, and 224d in this embodiment). The display device 222 can include an active area in which numerals, text, symbols, images, or a combination thereof can be displayed (refer, for example, to FIG. 2), which can be used to communicate a number of settings or menu options for the infusion pump system 10. For example, the display device 222 can be used to communicate medicinal delivery information 227, such as the basal delivery rate, a bolus dosage, a historical record of medicine delivered, the amount of medicine remaining in the cartridge 120, or the like. In another example, the display device 222 can be used to communicate time and date information 228, which can be used by the user to determine dosage schedules, bolus delivery times, meal times, or the like.

In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. Accordingly, when the controller device 200 is connected to the pump device 100, the user can be provided with the opportunity to readily monitor infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200, which is removably attached to the pump device 100, without the requirement of locating and operating a separate monitoring module.

Figure 4:
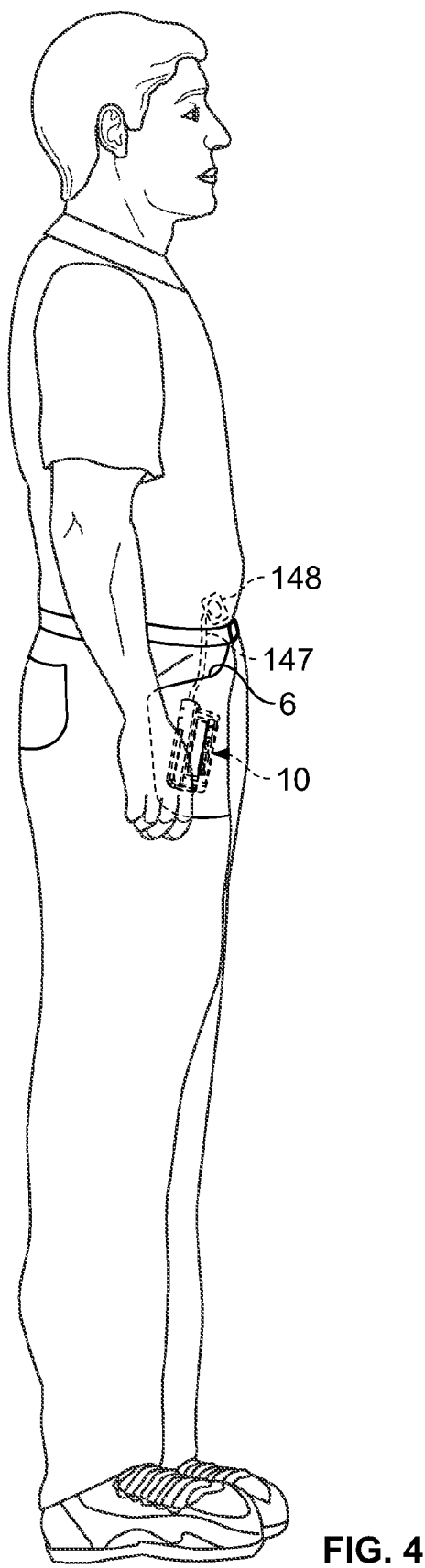
FIG. 4 is a perspective view of the infusion pump system worn on clothing of a user, in accordance with some embodiments.
Figure 5:
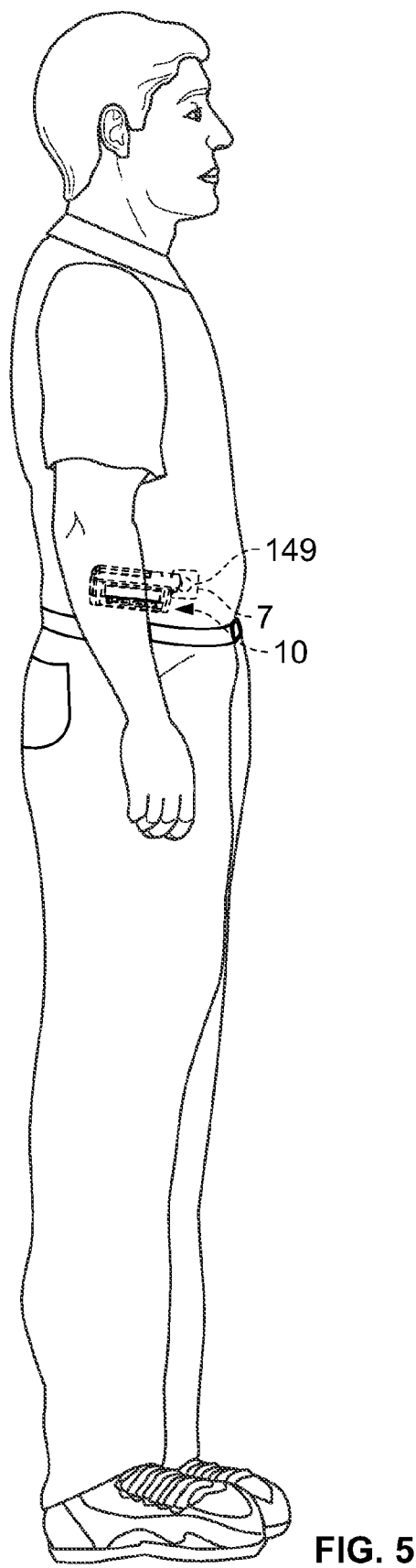
FIG. 5 is a perspective view of an infusion pump system worn on skin of a user, in accordance with particular embodiments.

Referring to now FIGS. 3-5, the infusion pump system 10 may be configured to be portable so that the user can readily carry or wear the pump system during operation. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. As described below in connection with FIG. 13, the drive system of the pump device 100 may be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in one embodiment). In addition, the pump housing structure 110 may have an overall height of about 2 cm to about 4 cm (about 3.1 cm or less in one embodiment) and an overall thickness of about 8 mm to about 20 mm (about 17.5 mm or less in one embodiment). In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump system 10 (including the removable controller device 200 attached to the pump device 100 having the cap 130) may have an overall length of about 7 cm to about 10 cm (about 9.3 cm or less in one embodiment), an overall height of about 2 cm to about 5 cm (about 4.2 cm or less in one embodiment), and an overall thickness of about 8 mm to about 20 mm (about 17.5 mm or less in one embodiment).

The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like). In such embodiments, the pump device 100 can deliver the medicine 126 through the infusion set 146.

As shown in FIG. 3, the infusion set 146 includes a tubing system that connects the infusion pump system 10 to the tissue or vasculature of the user (e.g., to deliver medicine into the tissue or vasculature under the user's skin). The infusion set 146 may include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 may provide fluid communication between the output end 122 (FIG. 2) of the medicine cartridge 120 and the tube 147 of the infusion set 146. For example, the tube 147 may be directly connected to an output port 139 (FIG. 2) of the cap device 130. In another example, the infusion set 146 may include a connector (e.g., a Luer connector or the like) attached to the tube 147, and the connector can then mate with the cap device 130 to provide the fluid communication to the tube 147. In these examples, the user can carry the portable infusion pump system 10 (e.g., in the user's pocket, connected to a belt clip, adhered to the user's skin, or the like) while the tube 147 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module In the event that an alarm condition (e.g., low power, low medicine volume, occlusion detection, drive system or electrical communication error, or the like) is detected by the pump system 10, the display device 222 can be used to communicate an alert to the user. If the pump system 10 detects an occlusion in the medicine flow path (which can cause inaccurate dosage delivery), an audible alert, in addition to or in place of the alert displayed on the device 222, can be used to notify the user of the detected occlusion. The audible alert may be in the form of an alert beep, a voice notification, or a combination thereof. In particular embodiments, the audible alert can include a voice notification that states: "Alert. An occlusion has been detected. Please check the infusion set for blockages." In addition, the display device 222 may provide a visual alert that indicates the detected alarm condition. In some examples, the user can acknowledge the alarm communication by pressing the button 224b adjacent to a "clear" command. Other alarm conditions may require further intervention by the user. In those situations, the audible alert may include voice instructions that indicate the actions to be performed by the user.

Referring to FIG. 4-5, a user can conveniently wear the infusion pump system 10 on the user's skin (e.g., through the use of skin adhesive) underneath the user's clothing or carry the pump device 100 in the user's pocket (or other portable location) while receiving the medicine dispensed from the pump device 100. As shown in FIG. 4, in some embodiments, the infusion pump system 10 is pocket-sized so that the pump device 100 and controller device 200 can be worn in a user's pocket 6 or in another portion of the user's clothing. For example, the pump device 100 and the controller device 200 can be attached together and form the system 10 that comfortably fits into a user's pocket 6. The user can carry the portable infusion pump system 10 and use the tube 147 of the infusion set 146 to direct the dispensed medicine to the desired infusion site. In some circumstances, the user may desire to wear the pump system 10 in a more discrete manner. Accordingly, the user may pass the tube 147 from the pocket 6, under the user's clothing, and to the infusion site where the adhesive patch 148 is positioned. As such, the pump system 10 can be used to delivery medicine to the tissues or vasculature of the user in a portable, concealable, and discrete manner.

Referring to FIG. 5, in other embodiments, the infusion pump system 10 may be configured to adhere to the user's skin 7 directly at the location in which the skin is penetrated for medicine infusion. For example, a rear surface (not shown) of the pump device 100 may include a skin adhesive patch so that the pump device 100 is physically adhered to the skin of the user at a particular location. In these embodiments, the cap device 130 (FIG. 2) may have a configuration in which medicine passes directly from the cap device 130 into an infusion cannula 149 that is penetrated into the user's skin. In one example, the fluid output port 139 (FIG. 2) through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220.

Referring now to FIGS. 6-11, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge 120 is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge 120 is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120'. Furthermore, the pump system 10 can provide the user with an opportunity to obtain a plurality of the pump devices 100 at the pharmacy 60 (FIG. 1) over a period of time.

Referring to FIGS. 6-7, the pump device 100 can be readily removed from the controller device 200 when the medicine cartridge 120 is exhausted. As previously described, the medicine cartridge 120 is inserted into the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length. Optionally, some embodiments of the pump device 100 may include a label 117a that is adhered around the barrel 111. The label 117a may provide a convenient location for basic user instructions, product identification information, and other information related to the infusion pump system 10. To provide enhanced viewability of the medicine cartridge 120 through the label 117a, the label 117a may include a window 117b through which the user may visually inspect if the plunger 125 is nearing the end of its travel length.

As shown in FIG. 6, the pump device 100 has been used to a point at which the medicine cartridge 120 is exhausted. The plunger 125 has been advanced, toward the left in FIG. 6, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 (and through the window 117b of the label 117a in this embodiment) to determine if the medicine cartridge 120 is almost empty. When the user determines that a new medicine cartridge 120 should be employed, the pump device 100 can be readily separated from the controller device 200 by actuating the release member 215. In this embodiment, the release member 215 is a latch on the controller device 200 that is biased toward a locking position to engage the pump device 100. The latch 215 may be arranged to engage one or more features on a lateral side of the pump housing 110. As such, the user may actuate the release member 215 by moving the release member 215 in a lateral direction 216 (FIG. 6) away from the pump device 100 (e.g., by applying a force with the user's finger).

As shown in FIG. 7, when the release member 215 is actuated and moved to a position away from the pump device 100, the segmented guide rail 114a-b is free to slide longitudinally in the guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213, and the electrical connector 118 can be separated from the mating connector 218. In these circumstances, the pump device 100 is physically and electrically disconnected from the controller device 200 while the pump device retains the exhausted medicine cartridge 120.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., move in the lateral direction 216 in the embodiment shown in FIG. 6). Accordingly, in some embodiments, the pump device 100 can automatically and sharply move a small distance (e.g., about 0.5 mm to about 5 mm) away from the controller 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 9:
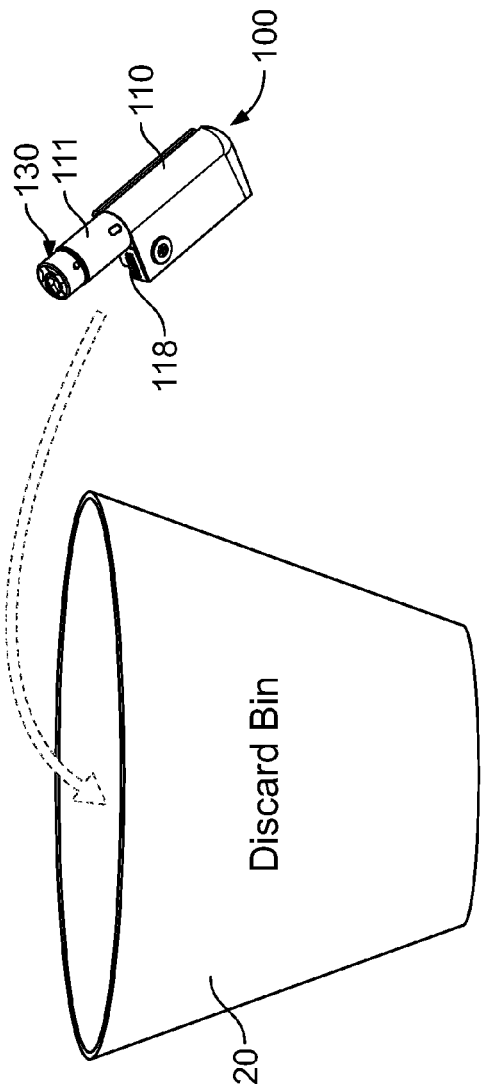

Referring to FIGS. 8-9, the same controller device 200 can be reused with the new pump device 100' having the new medicine cartridge 120' retained therein, and the previously used pump device 100 can be discarded with the exhausted medicine cartridge 120. As previously described in connection with FIG. 1, the user may obtain a plurality of the pump devices 100 from a single pharmacy transaction, so the new pump device 100' may be readily available to the user after exhaustion of the previous pump device 100. The new pump device 100' (FIG. 8) can have a similar appearance, form factor, and operation as the previously used pump device 100 (FIGS. 6-7 and 9), and thus the new pump device 100' can be readily attached to the controller device 200 for controlled dispensation of medicine from the new medicine cartridge 120'. In some embodiments, the user may prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 147 of the infusion set 146 is not shown in FIG. 8, it should be understood that the tubing 147 may be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller 200) before attaching the infusion set patch to the user's skin. As shown in FIG. 8, the new medicine cartridge 120' may be filled with medicine such that the plunger 125 is not viewable through the barrel 111.

As shown in FIG. 9, the previously used pump device 100 that was separated from the controller device (as described in connection with FIGS. 6-7) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 20, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 146 (not shown in FIG. 9, refer to FIG. 3) that was used with the pump device 100 may be removed from the user and discarded into the bin 20 along with the pump device 100. Alternatively, the infusion set 146 can be disconnected from the previous pump device 100 and attached to the new pump device 100'. In these circumstances, the user may detach the infusion set cannula and patch from the skin so as to "re-prime" the tubing with medicine from the new pump device 100' to remove air pockets from the tubing. Thereafter, the infusion set cannula and patch can be again secured to the user's skin.

Figures 10, 11:
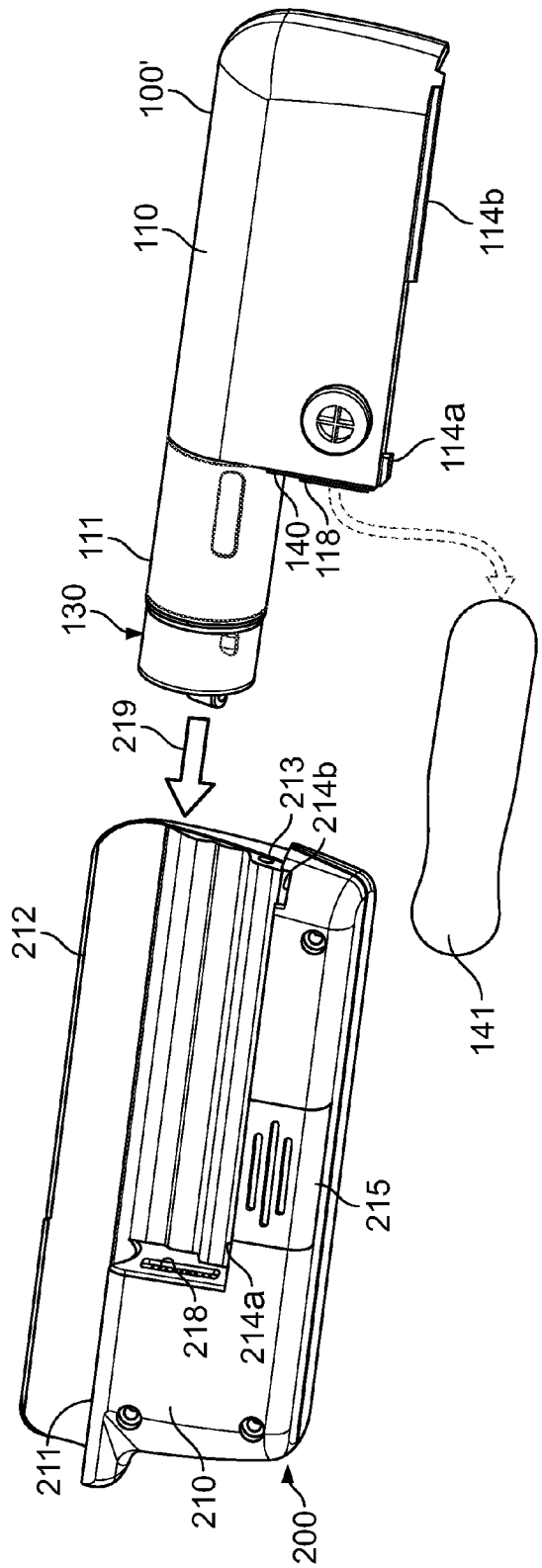
FIGS. 10-11 are perspective views of the new pump device of FIG. 8 being attached to the controller device of FIG. 8.

Referring to FIGS. 10-11, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling a removable tab 141 away from the pump housing 110. In this embodiment, the new pump device 100' includes the removable tab 141 to seal the battery in the unused pump device 100' and thereby maintain the battery in a storage mode (refer, for example, to FIG. 14 in which the removable tab 141 is arranged to cover an internal face of a vent 145). The vent 145 can be implemented in some embodiments of the infusion pump system 10 having a power source arranged that draws upon surrounding air for optimum operation. Because the controller device 200 and the pump device 100 may be sealed to resist water migration during normal usage, the water-resistant vent instrument 145 may be used to provide the air to the power source without permitting migration of water therethrough. For example, in this embodiment, the pump device 100 may house a power source 345 in the form of a zinc-air cell battery (refer to FIG. 13), which draws upon the surrounding air during operation. When the pump device 100 is in use, the pump housing 110 is preferably sealed to protect the internal drive system and medicine cartridge from water migration. As such, the pump housing 110 may include the water-resistant vent 145 disposed proximate to the zinc-air cell battery 345 so that some air may pass through the vent 145 and toward the battery. The water-resistant vent instrument 145 may include one or more layers of a material that is permeable to air and resistant to passage of liquids such as water. For example, the water-resistant vent instrument 145 may include one or more layers of a GORE-TEX material to resist the migration of water into the pump device while permitting the passage of air toward the battery.

As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

The new pump device 100' can be connected to the controller device 200 by advancing the new pump device 100' in a longitudinal direction 219 (FIG. 10) toward the controller device 200. When the pump device 100' is advanced in the longitudinal direction 219 toward the controller device 200, the movement is guided by the slider channel 112 (FIG. 2) and the segmented rails 114a-b. In particular, the slider channel 112 of the pump housing engages the rail 212 of the controller housing 210. Also, the front portion of the segmented rail 114a slides into the rear portion of the guide channel 214b. In this embodiment, the front portion of the segmented rail 114a includes a ramp surface 114c (refer also to FIG. 2) that engages a complementary ramp surface of the release member 215 to thereby force the release member 215 away from the guide channel 214a-b during advancement of the pump device 100'. The release member 215 is temporarily forced away from the guide channel 214a-b so that the front portion of the segmented rail 114a passes over the release member 215, which enables the electrical connector 118 of the pump device 100' to engage with the mating connector 218 of the controller device 200. As the connectors 118 and 218 join together to form the electrical connection, the release member 215 biased to return to its latched position and is shifted to a position in the guide channel 214a-b between the segmented rails 114a-b so as to prevent withdrawal of the pump device 100'.

As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 permits users to readily join the pump device 100' and the controller device 200 without compound or otherwise difficult hand movements—a feature that can be beneficial to child users or to elderly users.

As shown in FIG. 11, when the new pump device 100' is fully advanced and attached to the controller device 200, the gasket 140 is compressed between the opposing surfaces of the pump housing 110 and the controller housing 210. Such a configuration provides a water-resistance seal around the electrical connection that protects the sensitive internal components of the pump device 100' and the controller device 200 from damage or malfunction. As previously described in connection with FIG. 3, the tubing 147 of the infusion set 146 can be attached to the cap device 130 to provide a fluid path from the new pump device 100' to the user. Thus, the new pump device 100' can deliver medicine to the user under the control of the reusable controller device 200.

Figure 12:
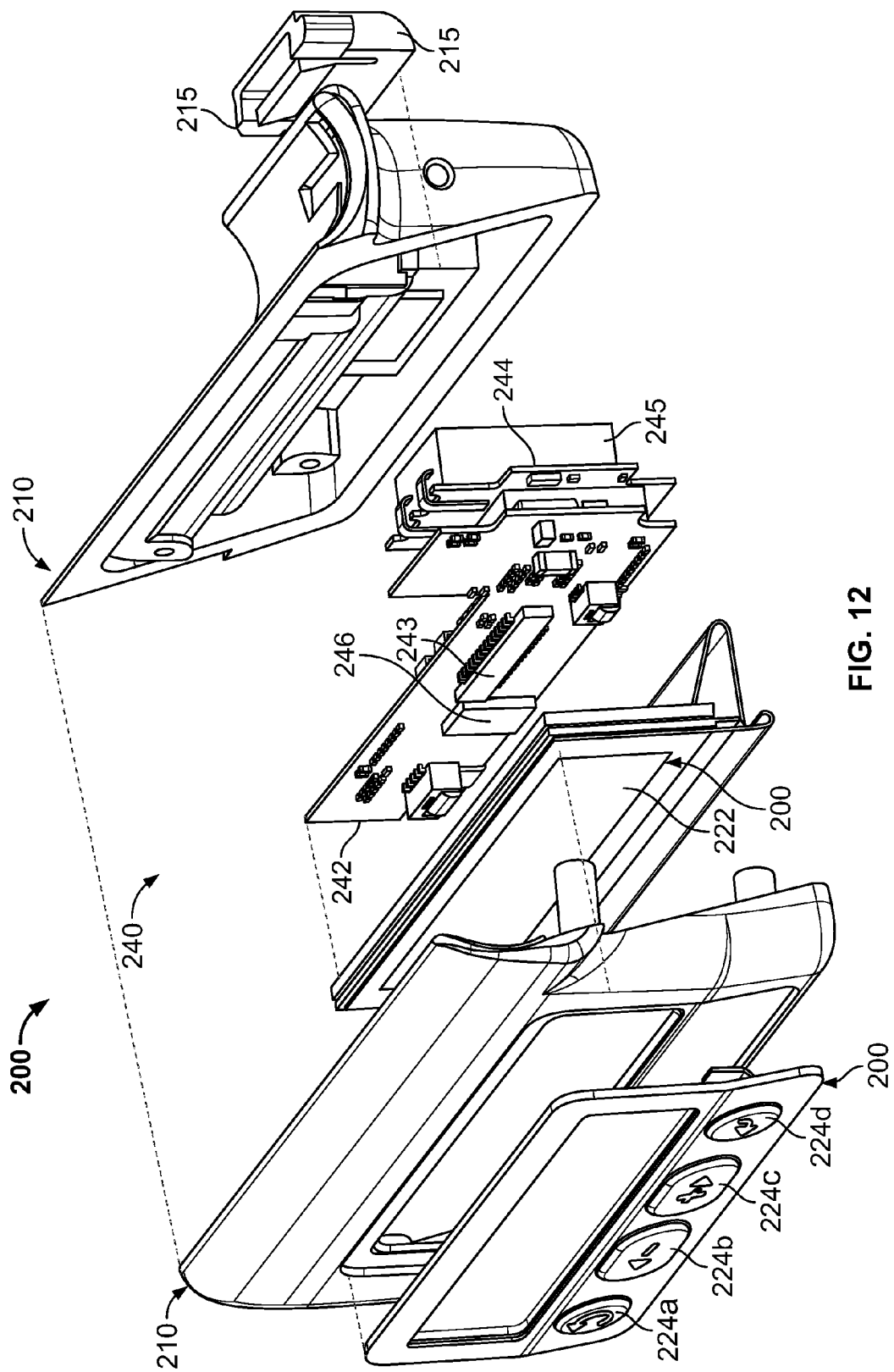
FIG. 12 is an exploded perspective view of a controller device for an infusion pump system, in accordance with some embodiments.

Referring now to FIG. 12, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as at least one memory device 246. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the memory device 246 arranged in the control circuitry 240. Furthermore, in some embodiments the memory device 246 can store executable software instructions for the processor 243. Alternatively, the control circuitry 240 may include other dedicated memory devices (e.g., separate from the memory device 246) that store executable software instructions for the processor 243. The control circuitry 240 may include other components, such as sensors, that are electrically connected to the main processor board 242. For example, at least a portion of an occlusion sensor system (not shown in FIG. 12) can be electrically connected to the main processor board 242 via a flexible circuit substrate or one or more wires.

As previously described, the controller device 200 can be electrically connected with the pump device 100 via mating connectors 118 and 218 (FIGS. 2 and 7) so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 7) on the controller device 200 is adapted to mate therewith. The electrical connector 218 on the controller device 200 is in communication with the control circuitry 240. As such, the processor 243 can operate according to software instructions stored in the memory device 246 so as to send control signals to the pump device 100 via the connector 218.

The memory device 246 may store infusion pump data, such as pump settings and menu options, basal and bolus dispensation data, executable software instructions (for the processor 243) that control the operation of the pump device 100, and the like. The memory device 246 can be selected to provide ample storage space for the infusion pump data so that the pump device 100 can safely dispense the medicine in accordance with the signals from the properly operating control device 200. In particular embodiments, the memory device 246 may have a portion that is partitioned or segregated from the other contents of the memory device 246 or otherwise protected from overwriting during the process of updating or changing the content in other portions of the memory device 246. In alternative embodiments, the memory device 246 may comprise a plurality of separate memory cards or memory chips accessible to the processor 243, some of which are dedicated to the infusion pump data.

Still referring to FIG. 12, the user interface 220 of the controller device 200 can include input components, output components, or both that are electrically connected to the control circuitry 240. For example, in this embodiment, the user interface 220 includes the display device 222 having an active area that outputs information to a user and four buttons 224$a$-$d$ that receive input from the user. Here, the display 222 may be used to communicate a number of settings or menu options for the infusion pump system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 10. Some embodiments of the pump system 10 include a cable connector (e.g., a data cable port or a data cable that mates with connector 218) for communicating with a separate computer system. As such, the data cable may electrically connect to the control circuitry 240 to upload data or program settings to the control circuitry 240 or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Still referring to FIG. 12, the control circuitry 240 of the controller device 200 may include a second power source 245 that can receive electrical energy from a first power source 345 (FIG. 13) housed in the pump device 100. In this embodiment, the second power source 245 is coupled to the power supply board 244 of the control circuitry 240. The hard-wired transmission of the electrical energy can occur through the previously described connectors 118 and 218 (FIGS. 2 and 7). In such circumstances, the first power source 345 (FIG. 13) may include a high density battery that is capable of providing a relatively large amount of electrical energy for its package size, while the second power source 245 (FIG. 12) may include a high current-output battery that is capable discharging a brief current burst to power a drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, as previously described, the first battery 345 may comprise a zinc-air cell battery. The zinc-air cell battery 345 may have a large volumetric energy density compared to some other battery types. For example, the zinc-air cell battery 345 may have a volumetric energy density of greater than about 900 Watt-hours/Liter (Wh/L), about 1000 Wh/L to about 1700 Wh/L, and about 1200 Wh/L to about 1600 Wh/L. Also, the zinc-air cell battery may have a long storage life, especially in those embodiments in which the battery is sealed (e.g., by the removable tab 141 or the like) during storage and before activation. One exemplary zinc-air cell battery provides a potential voltage of about 1.1V to about 1.6V (about 1.2V to about 1.4 V, and about 1.3 V in one embodiment), a current output of about 8 mA to about 12 mA (about 10 mA in one embodiment), and a storage capacity of greater than about 600 mA·h (about 650 mA·h in one embodiment).

As shown in FIG. 12, the second battery 245 may include a high current-output device that is housed inside the controller housing 210. The second battery 245 can be charged over a period of time by the first battery 345 and then intermittently deliver high-current bursts to the drive system 300 over a brief moment of time. For example, the second battery 245 may comprise a lithium-polymer battery. The lithium polymer battery disposed in the controller device 200 may have an initial current output that is greater than the zinc-air cell battery disposed in the pump device 100, but zinc-air cell battery may have an energy density that is greater than the lithium polymer battery (e.g., the lithium polymer battery disposed in the controller device 200 may have a volumetric energy density of less than about 600 Wh/L). In addition, the lithium-polymer battery 245 is readily rechargeable, which permits the zinc-air battery 345 disposed in the pump device 100 to provide electrical energy to the lithium-polymer battery 245 for purposes of recharging. One exemplary lithium-polymer battery provides a initial current output of about greater than 80 mA (about 90 mA to about 110 mA, and about 100 mA in one embodiment) and a maximum potential voltage of about 4.0V to and 4.4V (about 4.2 V in one embodiment). In other embodiments, it should be understood that the second power source 245 may comprise a capacitor device capable of being recharged over time and intermittently discharging a current burst to activate the drive system 300.

Accordingly, the infusion pump system 10 having two power sources 345 and 245—one arranged in the pump device 100 and another arranged in the reusable controller device 200—permits a user to continually operate the controller device 200 without having to recharge a battery via a wall-plug or other cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing (or possibly eliminating) the need for separate recharging of the controller device 200 via a power cord plugged into a wall outlet.

Figure 13:
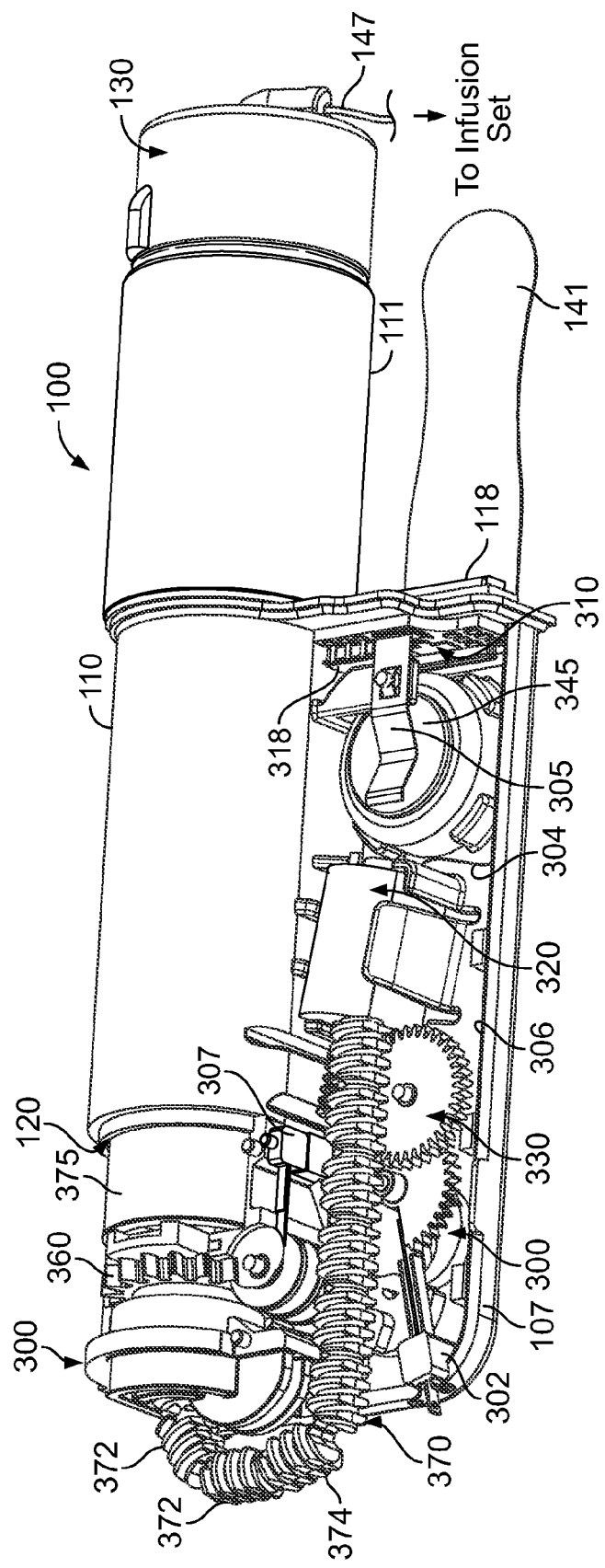
FIG. 13 is a perspective view of a pump device (with a housing portion removed) for an infusion pump system, in accordance with some embodiments.

Referring now to FIG. 13, the pump device 100 may include a drive system 300 that is controlled by the removable controller device 200 (FIGS. 1-3 and 8). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. In this embodiment, the pump housing 110 includes a chassis 107 that is at least partially covered by a shell portion (removed from FIG. 13 for purposes of illustrating the drive system 300). The shell portion can be used to cover at least a portion of the drive system 300. The shell portion can slide over and join with the chassis 107 (and other body portions) to form the assembled pump housing 110.

Some embodiments of the drive system 300 may include a battery powered actuator (e.g., a reversible motor 320 or the like) that resets a ratchet mechanism 330, a spring device 350 (FIG. 22) that provides the driving force to the ratchet mechanism 330, and a drive wheel 360 that is rotated by the ratchet mechanism 330 to advance the flexible piston rod 370 toward the medicine cartridge 120. Also, the pump device 100 can include one or more motion detectors coupled with the drive system 300 to provide feedback regarding the operation of the drive system 300. For example, the pump device 100 may include a first motion detector 302 configured as a limit switch that detects when a portion of the ratchet mechanism 330 has reached the limit of its travel and must thereafter stop movement or reverse direction. In another example, the pump device 100 may include a second motion detector 307 in the form of a mechanical error switch that indicates whether components of the drive system 300 completed the desired motion for each drive cycle.

Still referring to FIG. 13, the pump device 100 includes a connector circuit 310 to facilitate the transfer of signals to and from the electrical connector 118 (FIG. 1). As previously described, the electrical connector 118 of the pump device 100 mates with the connector 218 (FIG. 8) of the controller device 200 so that electrical communication can occur between the pump device 100 and the controller device 200. The connector circuit 310 may comprise a generally non-complex circuit 310 that does not include a processor or other relatively high-cost components. In this embodiment, the connector circuit 310 operates as a passageway for the control signals (from the control circuitry 240 (FIG. 12) of the controller device 200) to transmit to the drive system 300 (e.g., to the actuator 320). For example, the reversible motor 320 may be connected to the connector circuit 310 via one or more wires 304. The connector circuit 310 also operates as a passageway for the electrical power from the first battery 345 (FIG. 13) to pass to the controller device 200 for recharging of the second battery 245 (FIG. 12). For example, the first battery 345 may be connected to the connector circuit 310 via one or more power contacts 305. Furthermore, the connector circuit 310 operates as a passageway for feedback signals (e.g., from the motion detectors 302 and 307) to transmit to the control circuitry 240 (FIG. 12) of the controller device 200. For example, the limit switch 302 may be connected to the connector circuit 310 via one or more wires 306 (the one or more wires connecting the mechanical error switch 307 to the connector circuit 310 are not shown in FIG. 13).

In some embodiments, the connector circuit 310 in the pump device 100 includes a memory device 318 that can store data regarding the pump device 100 and its operational history. For example, the memory device 318 of the connector circuit 310 may include a flash memory chip that is configured to store data such as: a unique serial number designated for the pump device 100, a manufacturer identifier code, and a drive cycle counter. The unique serial number designated for the pump device 100 and the manufacturer identifier code may be useful pieces of quality control information that remains with the pump device 100 throughout its shelf-life and operational life. If, for example, a manufacturing error is identified for a particular pump device 100, the unique serial number and the manufacturer identifier code (e.g., a lot code) can be used to promptly identify the manufacturing location and its manufacturing lot.

The drive cycle counter stored in the memory device 318 can be useful for maintaining an accurate estimate of the volume of medicine that remains in the medicine cartridge 120. For example, the number of drive cycles that are required to incrementally advance the plunger 125 and thereby dispense a full medicine cartridge 120 may be a predetermined value (e.g., in some embodiments, 6,300 drive cycles result in full dispensation of a new medicine cartridge). Accordingly, the drive cycle counter stored in the memory device 318 can keep track of the number of drive cycles that have occurred through the operational life of the pump device 100. Each time the motor 320 completes a new drive cycle and incrementally advances the piston rod 370 to dispense some medicine, the controller device 200 can store an updated value for the drive cycle counter stored in the memory device 318. When the updated value stored in drive cycle counter stored in the memory device 318 approaches the predetermined value, the controller device 200 can alert the user that the medicine cartridge is approaching exhaustion. Furthermore, because the memory device 318 is arranged in the pump device 100, the drive cycle counter stored in the memory device 318 remains local to the pump device 100. If the pump device 100 is temporarily disconnected from the controller device 200 and then reconnected (or reconnected to a different controller device 200), the controller device 200 can retrieve the value for the drive cycle counter stored in the memory device 318 and promptly ascertain how much medicine remains in the medicine cartridge 120.

Still referring to FIG. 13, in some embodiments, the flexible piston rod 370 comprises a plurality of segments 372 serially connected by hinge portions 373 so that the flexible piston rod 370 is adjustable from a curved shape to a noncurved shape. The plurality of segments 372 and the interconnecting hinge portions 373 can be integrally formed in one piece from one or more moldable materials, including polymer materials such as Nylon or POM. In this embodiment, each of the plurality of rod segments 372 includes an exterior thread pattern 374 along at least one cylindrical surface portion. The piston rod 370 also includes a plunger engagement device 375 can be arranged at a forward end of the piston rod 370. As such, the plunger engagement device 375 faces toward the medicine cartridge 120 when the medicine cartridge 120 is inserted into the cavity 116. In some embodiments, the plunger engagement device 375 may comprise a pusher disc that abuts against the plunger 125 of the medicine cartridge 120.

Because the flexible piston rod 370 is adjustable from a curved shape to a noncurved shape, the overall length of the pump device can be reduced in some embodiments. For example, in a typical infusion pump that houses a straight and rigid rod, the typical infusion pump requires a package or housing having a linear dimension sufficient to accommodate the length of the rigid piston rod when it is at its limit of travel in which it is fully withdrawn from the container or cylinder. The pump device 100 incorporating the flexible piston rod 370 can require less space than a similar device that houses a non-flexible, rigid rod.

Accordingly, the pump device 100 is configured to removably attach to the controller device 200 in a manner that provides a secure fitting, an overall compact size, and a reliable electrical connection. When the pump device 100 and the controller device 200 are arranged in this attached configuration, the controller device 200 can be electrically connected with the pump device 100 to control operations of the pump drive system 300.

Figure 14:
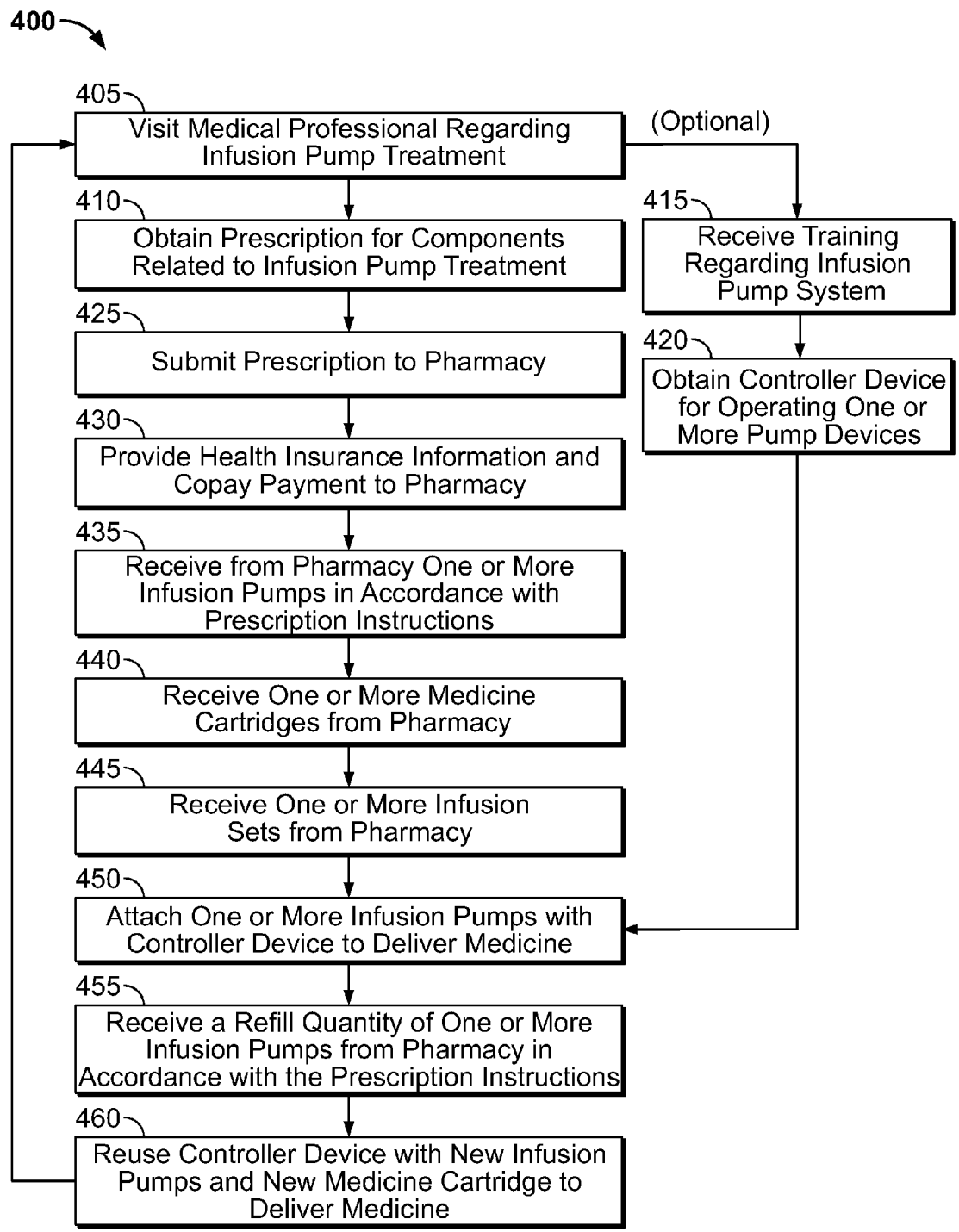
FIG. 14 is a flow diagram depicting the distribution of infusion pumps from the perspective of a user, in accordance with some embodiments.

Referring now to FIG. 14, some embodiments of a process 400 for obtaining an infusion pump can include a number of operations performed by a pump user. In operation 405, a patient visits a medical professional, such as a doctor, regarding a medical condition (e.g., diabetes, or another condition that can be treated through the use of an infusion pump system). During the visit, the doctor or other professional may determine that the patient is suitable for infusion pump therapy. Thereafter, in operation 410, the patient may obtain a prescription for components related to infusion pump therapy. For example, as previously described in connection with FIG. 1, the patient can receive a prescription 52 that indicates the use of one or more infusion pumps 100 and one or more medicine cartridges 120. It should be understood that the prescription 52 may be in the form of instructions to use the infusion pumps 100 even if a formal written prescription is not necessary to obtain the pumps 100 (e.g., if the pumps are available as over-the-counter products). The number of pump devices 100 that are prescribed in the operation 410 can be based on multiple factors, such as severity of the condition being treated, length of time that the pump device 100 is predicted to last for the patient, the length of time expected between visits to the pharmacy, the number of pump devices 100 permitted for a single transaction by the health insurance provider, and the like. The number of fluid cartridges 120 and infusion sets 146 that are prescribed can depend on the number of pump devices 100 that are prescribed. For example, the number of medicine cartridges 120 prescribed may be in a 1:1 ratio to the number of pump devices 100.

In some circumstances, the patient may not already possess particular components of the pump system, such as the reusable controller 200 that is not necessarily part of a refillable prescription. Optionally, in operation 415, the patient may attend a training session regarding use of the infusion pump system. In some embodiments, this training session takes place at a time prior to the patient receiving the disposable components of the pump system 10. The training session can take place using a controller 200 used specifically for training purposes in which case the patient can acquire his/her own controller 200 (in operation 420) after attending the training session. Alternatively, the patient may receive his or her controller 200 for use during the training session. In addition, or in the alternative, the patient can attend a training session after acquiring all components of the pump system 10 so that the user may not only be instructed on proper use of the pump system 10, but can also configure the system 10 for use and begin receiving treatment from the pump system 10 before leaving the training session.

Returning now to portion of the process 400 after obtaining the prescription, in operation 425 the patient can submit the prescription information to a pharmacy. Optionally, in operation 430, the patient also submits health insurance information to the pharmacy so that the patient's health insurance will cover a portion of the costs for the infusion pumps, medicine, or both. As previously described in connection with FIG. 1, the user may be required to pay only a copay payment to the pharmacy for the costs not covered by the health insurance provider. In some cases, the entire cost of the disposable portions of the pump system 10 will be covered, thus eliminating the need for the patient to supply a copay payment in the operation 430. In some examples, the prescription, health insurance, and copay can all be provided at the same time. In other examples, these three items can be provided at any time and in any order. For example, the patient may be a regular customer of the pharmacy, thus the patient's health insurance information may already be on file in the pharmacy, thus eliminating the need for the patient to supply health insurance information during the operation 430. In still other examples, the patient may not have health insurance that will cover the costs of the pump system 10, thereby eliminating the need for the patient to supply health insurance information to the pharmacy. In these cases, the payment made by the patient to the pharmacy is in place of a copay payment and represents the entire cost of the portions of the pump system 10 received.

When the proper information and payments have been provided to the pharmacy, the patient receives from the pharmacy (in operation 435) one or more pump devices 100. In operation 440, the patient may also receive one or more fluid cartridges 120 from the pharmacy. In some embodiments, the number of cartridges 120 can be provided in a 1:1 ratio with the number of infusion pumps 100. In operation 435, the patient can receive one or more infusion sets 146 from the pharmacy. As previously described in connection with FIG. 1, the operations 425-445 can take place, for example, in a brick and mortar establishment, or can take place via direct order pharmacy system in which the information is provided from the patient to the pharmacy over the phone or Internet, and the components of the system 10 are sent to the patient's address. In operation 450, the patient couples the pump device 100, fluid cartridge 120, and infusion set 146 to the controller device 200 to thereby provide controlled infusion of the medicine.

Still referring to FIG. 14, in operation 455, the patient may receive a refill quantity from the pharmacy. This may occur, for example, after the patient uses a quantity of the disposable components of the pump system 10 (e.g., one or more pump devices 100, one or more fluid cartridges 120, and one or more infusion sets 146). In some embodiments, the prescription obtained by the patient can indicate a maximum time limit or number of times that the prescription for the infusion pumps can be refilled. When appropriate, the patient can contact the pharmacy, provide an additional copay payment if applicable, and receive the refill quantity of pump devices 100', fluid cartridges 120', and/or infusion sets 146' as indicated by the prescription instructions. In operation 460, the patient can reuse the controller device 200 with the new infusion pump 100 and new medicine cartridges 120. For example, as described in connection with FIGS. 6-11, when the pump system 10 has exhausted the supply of medicine in the cartridge 120, the patient can discard the disposable pump device 100 and replace it with the new pump device 100', fluid cartridge 120', and infusion set 146'. If the number of times that the prescription has been refilled or the refill time period has equaled or exceeded the maximum amount indicated on the prescription, the patient may visit the medical professional (or another medical professional) for a check-up and new prescription. As such, the process 400 may return to operation 405 to receive a new prescription for the infusion pumps and other components (e.g., medicine cartridges 120) of the pump system 10.

Figure 15:
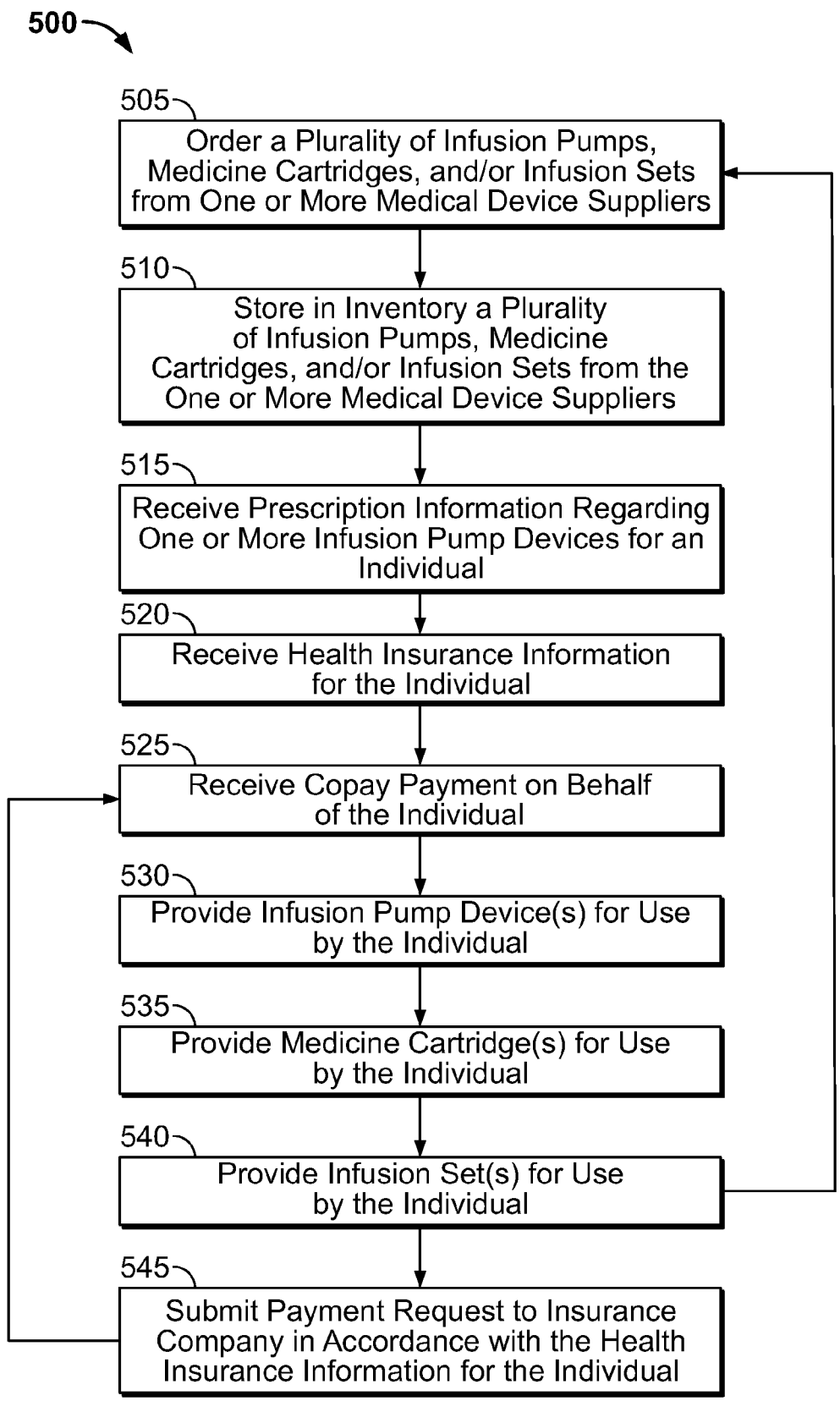
FIG. 15 is a flow diagram depicting the distribution of insulin pumps from the perspective of a pharmacy, in accordance with some embodiments.

Referring now to FIG. 15, some embodiments of a process 500 for distributing infusion pumps can include a number of operations in a pharmacy system. In operation 505, a pharmacy may order a plurality of infusion pump components, such as the pump devices 100, the fluid cartridges 120, and/or the infusion sets 146. In some embodiments, the pharmacy can receive these components from one or more suppliers available to the pharmacy. For example, the pharmacy can order the pump devices 100 from a single supplier, the fluid cartridges 120 from four suppliers, and the infusion sets 146 from two different supplier.

In operation 510, the pharmacy receives the previously ordered components and stores the components in its inventory. In particular, the plurality of infusion pumps 100, the plurality of medicine cartridges 120, and the plurality of infusion sets 146 can be stored in the pharmacy inventory according to instructions supplied by manufacturer(s) of the components. For example, the medicine cartridges 120 may be stored in a refrigerated environment, while the pump devices 100 and the infusion sets 146 are stored at substantially room temperature. In another example, the components can be received from a supplier in prepackaged kits (described below in connection with FIGS. 16-17) and stored collectively in a single location. In still another example, a predetermined number of the items received from the medical suppliers can be packaged by the pharmacy into the infusion pump kits.

Still referring to FIG. 15, in operation 515 the pharmacy may receive prescription information from a customer regarding one or more infusion pump devices 100 and other components (e.g., medicine cartridges 120). As previously described in connection with FIG. 1, the prescription information received can instructions related to a number of pump devices 100, fluid cartridges 120, and (optionally) infusion sets 146 that have been prescribed by a medical professional. The prescription information may also indicate the maximum refill time period or maximum number of times that the prescription can be refilled. The prescription can be saved by the pharmacy so that in the future, the pharmacy may provide one or more refill quantities of the prescription without having to require that the customer provide this information again. It should be understood that, in some embodiments, the prescription information may include written instructions from a medical professional for the use of infusion pumps or components that do not require a formal written prescription. In some embodiments, the number of cartridges 120 prescribed in the prescription information may be in a 1:1 ratio with the number of pump devices 100.

In operation 520, the pharmacy may optionally receive health insurance information (e.g., an insurance card or the like) from the customer. The health insurance information can provide information about the customer's health care coverage (e.g., contact information for the health insurance provider, a customer identifier, and the like), which can be saved by the pharmacy for future use when the customer returns for a refill quantity of the prescription. In operation 525, the pharmacy may receive a copay payment from the customer to cover the costs of the components in the prescription that are not covered by the health insurance provider. It should be understood from the description herein that the prescription, health insurance information, and copay can be received by the pharmacy contemporaneously or at different points in time.

Still referring to FIG. 15, in operation 530, the pharmacy provides to the customer one or more infusion pumps. As previously described in connection with FIG. 1, the infusion pumps may include disposable pump devices 100 configured to infuse medicine to a user. In operation 535, the pharmacy may provide one or more medicine cartridges 120 to the customer. Also, in operation 540, the pharmacy may provide one or more infusion sets 146 to the customer. In one example, the pharmacy can provide the pump devices 100, medicine cartridges 120, and infusion sets 146 as described in association with the transaction 65 described in FIG. 1. In operation 545, the pharmacy submits a payment request to the customer's health insurance provider in accordance with the health insurance information to receive payment for the portion of the costs covered by the health insurance company.

After a period of time, the process 500 may return to operation 525 in which the pharmacy receives a copay payment from the customer with the expectation of providing the customer with a refill quantity of one or more of the infusion pumps or other components described in the prescription information. When the customer returns for a refill quantity, the pharmacy can check a customer record to verify that there is valid prescription information on file and that the maximum refill time and number of refills have not been exceeded. The pharmacy may also verify that the health insurance information remains valid and that the costs of the refill quantity will be covered by the health insurance provider. As described previously in connection with operations 530-540, the pharmacy provides the prescribed components (e.g., one or more pump devices 100, one or more fluid cartridges 120, and/or one or more infusion sets 146) to the customer as part of the refill transaction. In some embodiments, after delivering the prescribed components (as in operations 530-540), the pharmacy updates the customers record to indicate that that a refill quantity has been given (e.g., incrementing a counter representing the number of times the prescription has been refilled). The pharmacy may repeat operations 525-540, receiving from the customer the required copay payment and providing refill quantities to the customer, as long as the maximum refill time period or number of refills is not exceeded and the health insurance provider authorizes the refill quantity. After a maximum refill time period or number of refills is exceeded, the pharmacy may request that the customer submits a new prescription to the pharmacy.

At a subsequent point in time (e.g., at regular intervals, after delivering components of the pump system 10 to a customer, when the inventory of one or more components of the pump system 10 become low, and the like) the pharmacy may evaluate the existing inventory. Accordingly, the process 500 may return to operation 505 in which the pharmacy again orders additional quantities of the infusion pumps or other related components. The additional quantities can be used to replenish the pharmacy inventory.

Figure 16:
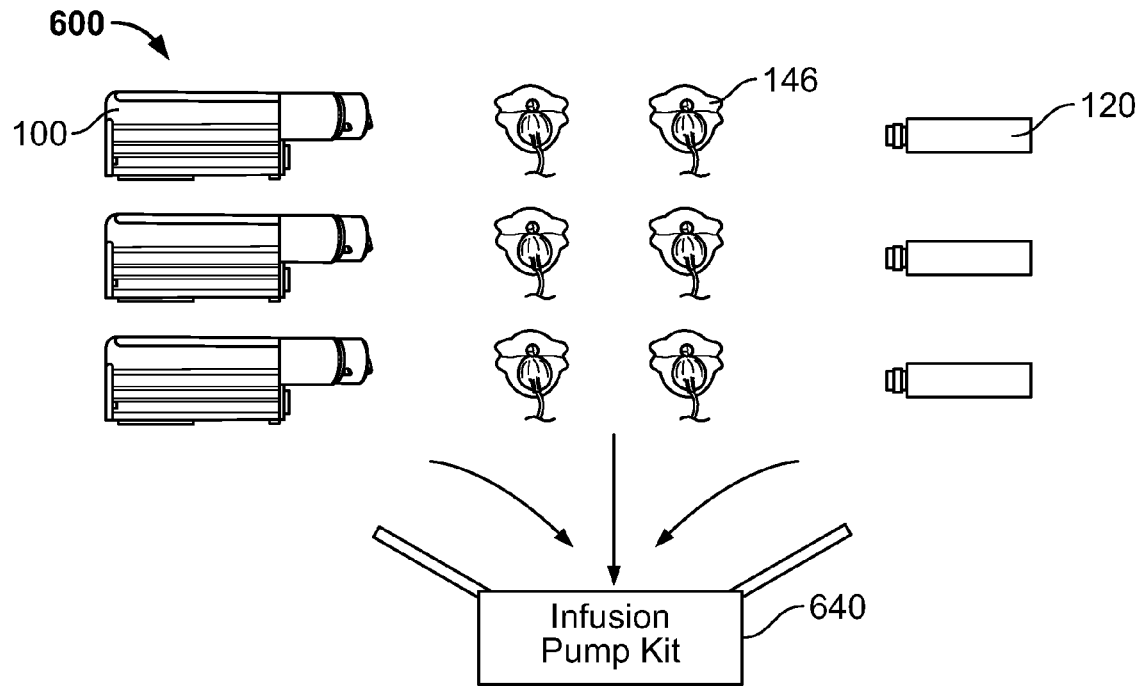
FIG. 16 depicts the contents of an infusion pump kit prior to packaging, in accordance with some embodiments.
Figure 17:
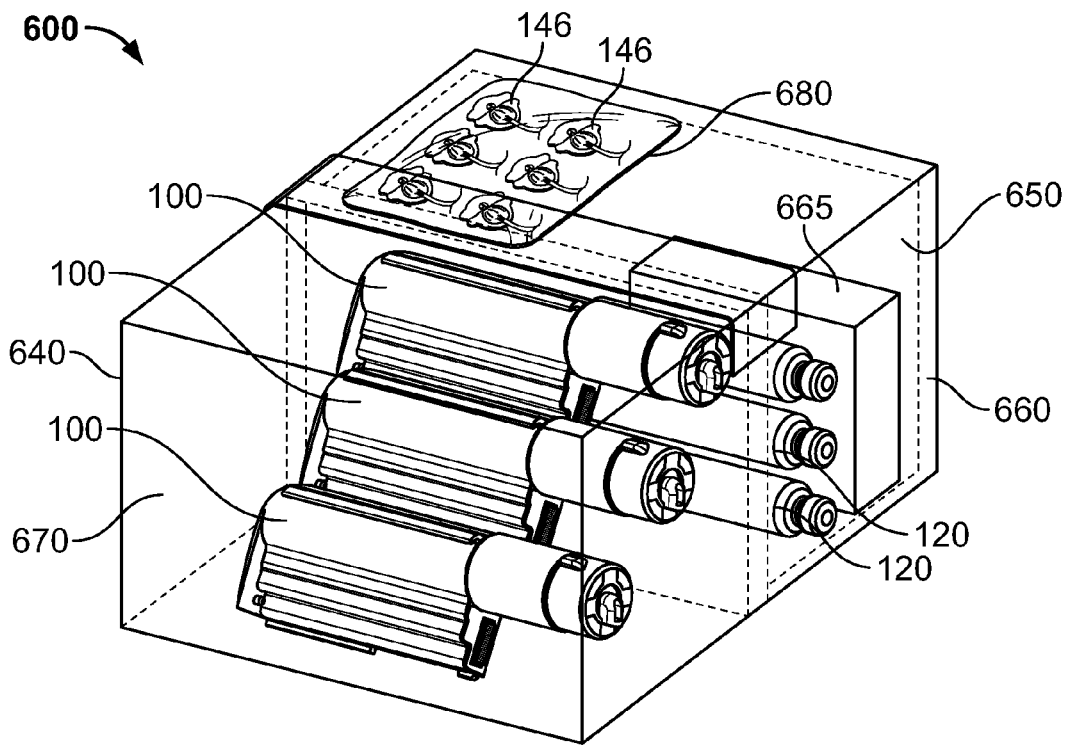
FIG. 17 is a perspective view of the infusion pump kit depicted in FIG. 16 after packaging, in accordance with some embodiments.

Referring to now FIG. 16-17, in some embodiments the infusion pumps can be packaged together with other components in an infusion pump kit 600. The infusion pump kit 600 can include one or more pump devices 100, one or more medicine cartridges 120, and (optionally) one or more infusion sets 146 that are packaged in predetermined numbers for convenient distribution to pump users. In this embodiment, the infusion pump kit 600 may include a container 640, three pump devices 100, three medicine cartridges 120, and six infusion sets 146. Accordingly, the quantity of infusion pumps 100 provided in the container 640 is in a 1:1 ratio with the quantity of medicine cartridges 120 provided in the container 640. It should be understood that, in other embodiments, the kits 600 can include other quantities of pump devices 100 (e.g., 1, 2, 4, and the like), medicine cartridges 120, and infusion sets 146. For example, the kit 600 can include two pump devices 100, two medicine cartridges 120, and three infusion sets 146.

In some embodiments, the one or more pump devices 100, the one or more fluid cartridges 120, and/or the one or more infusion sets 146 are assembled into the infusion pump kit 600 by a medical device supplier for shipment to a pharmacy. In alternative embodiments, a pharmacy can receive the individual components of the pump system 10 from one or more medical device suppliers and assemble these items into the kit 600 at the pharmacy for subsequent distribution to customers.

Referring to FIG. 17, the container 640 of the infusion pump kit 600 can include separate compartments for storage of the different pump system 10 components. In some embodiments, the container 640 includes an insulated compartment 650 surrounded by thermal insulation 660 for maintaining the three medicine cartridges 120 in a refrigerated state suitable for storage of medicine during transport. Additionally, the compartment 650 can include a cold pack 665. The thermal insulation 660 and the cold pack 665 can be configured to maintain the medicine cartridges 120 in a refrigerated state during the distribution time to the pump user. For example, in the embodiments in which the medicine cartridges 120 contain insulin, the thermal insulation 660 and the cold pack 665 can be configured to maintain the medicine cartridges 120 at less than about 55° F., less than about 50° F., less than about 45° F., between about 33° F. and about 44° F., and preferably between 35° F. and 39° F.) In some embodiments, the cold pack 665 may comprise a gel pack that can be cooled by placement in a refrigerator or freezer. After cooling, the cold pack 665 can be placed in the compartment 650 to help maintain the temperature of the compartment 650 within the desired range. In another example, the cold pack 665 can be a chemical pack that, when chemicals inside the pack are mixed, cause the temperature of the chemical pack to fall. A second compartment 670 of the container 640 can store the pump devices 100. This compartment 670 is not necessarily insulated and may remain at ambient temperatures during transport. In some circumstances, the first and second compartments 650 and 670 may include packaging material such as foam material or bubble-wrap. The container 640 may also contain a number of infusion sets 146. The infusion sets 146 can be arranged in a sealed pouch 680 so as to maintain the infusion sets 146 in a sterile condition during distribution to the pump user. It should be understood that, in alternative embodiments, the container 640 can contain quantities of pump devices 100, medicine cartridges 120, and (optionally) infusion sets 146 that are different from those quantities depicted in FIGS. 16-17.

A number of embodiments of the invention have been described. Nevertheless, it will be understood that various modifications may be made without departing from the spirit and scope of the invention. Accordingly, other embodiments are within the scope of the following claims.

What is claimed is:

1. A method of providing a medicine infusion pump device, comprising:

storing multiple infusion pump devices in a pharmacy inventory while also storing prefilled medicine cartridges in the pharmacy inventory, each of the prefilled medicine cartridges being sealed by a pierceable septum and being external to the infusion pump devices when stored in the pharmacy inventory, each of the infusion pump devices including a cap device configured to seal an external opening of a respective infusion pump device and configured to pierce the septum of a respective prefilled medicine cartridge after the respective prefilled medicine cartridge is slidably inserted through said external opening; and in response to a request for a pharmacy to provide at least infusion pumps for an individual user, contemporaneously distributing from the pharmacy a set of said infusion pump devices in a predetermined quantity along with the same predetermined quantity of said prefilled medicine cartridges from the pharmacy inventory and a plurality of infusion sets attachable to said cap devices of the infusion pump devices, wherein the prefilled medicine cartridges are external to the infusion pump devices when the infusion pump devices are distributed to the individual user.

2. The method of claim 1, wherein the step of distributing the plurality of infusion pump devices comprises contemporaneously distributing the predetermined quantity of the infusion pump devices, the same predetermined quantity of the prefilled medicine cartridges, and the infusion sets in a kit that is equipped with a thermally insulated compartment configured to contain at least said predetermined quantity of the prefilled medicine cartridges.

3. The method of claim 2, wherein the kit distributed from the pharmacy includes the predetermined quantity of infusion pump devices, the predetermined quantity of prefilled medicine cartridges, and the infusion sets in a ratio of 1:1:2 respectively.

4. The method of claim 2, the kit distributed from the pharmacy includes a means for cooling said insulated compartment during transport of said kit.

5. The method of claim 1, further comprising contemporaneously receiving a payment on behalf of said individual user as part of a single transaction when distributing the plurality of infusion pump devices, the medicine cartridges, and the infusion sets.

6. The method of claim 1, wherein each of the infusion pump devices in said predetermined quantity of infusion pump devices is configured to removably attach to a reusable controller device having a user interface display so that any of said infusion pump devices that is attached to said reusable controller device is mechanically coupled with the user interface display of the reusable controller device.

7. The method of claim 6, each of the infusion pump devices in said predetermined quantity of infusion pump devices is configured to removably attach to a reusable controller device such that a first electrical connector exposed along an exterior of a selected infusion pump device with a second electrical connector exposed along an exterior of the reusable controller device.

8. The method of claim 1, wherein each of the infusion pump devices in said predetermined quantity of infusion pump devices includes a drive system comprising a rotational motor coupled to a gear system, the drive system being configured to dispense medicine from a corresponding one of said predetermined quantity of prefilled medicine cartridges.

9. The method of claim 1, further comprising distributing a refill set of infusion pump devices from the pharmacy in response to receiving a request for a refill set of infusion pump devices for said individual user, the refill set of infusion devices being contemporaneously distributing from the pharmacy along with a refill set of said prefilled medicine cartridges from the pharmacy inventory and a refill set of the infusion sets.

10. A method of providing an insulin infusion pump system, comprising:

arranging a plurality of disposable and non-reusable infusion pump devices and a plurality of prefilled insulin cartridges into a package according to a predetermined ratio of one infusion pump device to one prefilled insulin cartridge, each of the prefilled insulin cartridges being sealed by a pierceable septum and being external to the infusion pump devices arranged in the package, each of the infusion pump devices including a cap device configured to seal an external opening of a respective infusion pump device and configured to pierce the septum of a respective prefilled insulin cartridge after the respective prefilled insulin cartridge is slidably inserted through said external opening, wherein the prefilled insulin cartridges are positioned in an insulated cooler compartment of the package, and wherein the prefilled insulin cartridges are external to the infusion pump devices when the infusion pump devices are arranged into the package; and providing the package containing the predetermined ratio of the disposable and non-reusable infusion pump devices and the prefilled insulin cartridges to a requester in response to a request, wherein the prefilled insulin cartridges are external to the infusion pump devices when the infusion pump devices are distributed to the requester.

11. The method of claim 10, further comprising:

storing the infusion pump devices in a pharmacy inventory of a pharmacy while refrigerating the prefilled insulin cartridges in a refrigeration unit of the pharmacy inventory;

receiving at the pharmacy a prescription indicative of at least infusion pump devices for the requester, wherein the step of arranging the infusion pump devices and the prefilled insulin cartridges into the package is performed at the pharmacy after receiving at the pharmacy the prescription.

12. The method of claim 11, further comprising distributing a refill set of infusion pump devices from the pharmacy in response to receiving a request to refill said prescription for said requester, the refill set of infusion devices being contemporaneously distributing from the pharmacy along with a refill set of said prefilled medicine cartridges from the pharmacy inventory.

13. The method of claim 10, further comprising arranging a plurality of infusion sets into the package with the disposable and non-reusable infusion pump devices and insulin cartridges, wherein two or more infusion sets are arranged in the package for each one of the infusion pump devices arranged in the package.

14. The method of claim 10, further comprising contemporaneously receiving a payment on behalf of said requester as part of a single transaction when providing the package containing the predetermined ratio of the disposable and non-reusable infusion pump devices and the prefilled insulin cartridges to the requester.

* * * * *

UNITED STATES PATENT AND TRADEMARK OFFICE
CERTIFICATE OF CORRECTION

PATENT NO.        : 9,141,765 B2                    Page 1 of 1
APPLICATION NO.   : 14/032676
DATED             : September 22, 2015
INVENTOR(S)       : Mark C. Estes It is certified that error appears in the above-identified patent and that said Letters Patent is hereby corrected as shown below:

Title page, item (71) (Applicant), delete "Asante Solutions, Inc.," and insert -- Bigfoot Biomedical, Inc., --, therefor.

Title page, item (71) (Applicant), delete "Sunnyvale," and insert -- Milpitas, --, therefor.

Title page, item (56) (U.S. Patent Documents), delete "Mahoney" and insert -- Flaherty et al. --, therefor.

Specification

Column 1, line 7, delete "Jun. 27, 2013," and insert -- Jun. 27, 2012, --, therefor.

Signed and Sealed this
Twenty-second Day of March, 2016

Michelle K. Lee
*Director of the United States Patent and Trademark Office*